US007614036B2

(12) United States Patent
Bjornson et al.

(10) Patent No.: US 7,614,036 B2
(45) Date of Patent: Nov. 3, 2009

(54) METHOD AND SYSTEM FOR DATAFLOW CREATION AND EXECUTION

(76) Inventors: Robert D Bjornson, 159 Bradley St., New Haven, CT (US) 06511; Stephen B. Weston, 89 Carleton St., Hamden, CT (US) 06517; James D. Wing, 265 College St., Apt. 3D, New Haven, CT (US) 06510; Andrew H. Sherman, 1 Crestview Dr., North Haven, CT (US) 06473; Nathan L. H. Willard, 175 Mansfield St., Apt. 2, New Haven, CT (US) 06511; James McCusker, 3 Burlwood Dr., Burlington, CT (US) 06013

( * ) Notice: Subject to any disclaimer, the term of this patent is extended or adjusted under 35 U.S.C. 154(b) by 1020 days.

(21) Appl. No.: 10/610,133

(22) Filed: Jun. 30, 2003

(65) Prior Publication Data

US 2004/0056908 A1 Mar. 25, 2004

Related U.S. Application Data

(63) Continuation-in-part of application No. 09/814,056, filed on Mar. 22, 2001, now Pat. No. 6,691,109.

(51) Int. Cl.
*G06F 9/45* (2006.01)
(52) U.S. Cl. .................................... 717/105
(58) Field of Classification Search ......... 717/105–139; 716/1
See application file for complete search history.

(56) References Cited

U.S. PATENT DOCUMENTS

| 5,555,201 | A | * | 9/1996 | Dangelo et al. ............ 716/1 |
|---|---|---|---|---|
| 5,625,823 | A | * | 4/1997 | Debenedictis et al. ....... 717/139 |
| 5,701,256 | A | | 12/1997 | Marr et al. |
| 5,828,894 | A | | 10/1998 | Wilkinson et al. |
| 5,873,052 | A | | 2/1999 | Sharaf |
| 5,884,303 | A | | 3/1999 | Brown |
| 5,999,729 | A | * | 12/1999 | Tabloski et al. ............. 717/105 |
| 6,009,422 | A | | 12/1999 | Ciccarelli |
| 6,088,044 | A | | 7/2000 | Kwok et al. |
| 6,112,225 | A | | 8/2000 | Kraft et al. |

(Continued)

OTHER PUBLICATIONS

Camp, "High-Throughput Blast," Silicon Graphics, Inc., 15 pp (Sep. 1998).

(Continued)

*Primary Examiner*—John Chavis
(74) *Attorney, Agent, or Firm*—Stolowitz Ford Cowger LLP

(57) ABSTRACT

A method, apparatus and tangible medium for creating and executing a computer dataflow. A plurality of components is defined, each representing a computer-implemented computational process that is performed on one or more inputs and that generates one or more outputs. A graphical user interface is provided allowing a user to visually create the computer dataflow on a user display by selecting from a library of components, connecting the component's input terminals with output terminals. The input terminals graphically correspond to inputs to the component's predefined computational algorithm and the output terminals graphically correspond to outputs generated by the component's predefined computational algorithm. Without user intervention, the plurality of said selected components is distributed for execution across a plurality of machines and automatically executes upon receiving a minimum number of inputs.

46 Claims, 21 Drawing Sheets

U.S. PATENT DOCUMENTS

| | | | |
|---|---|---|---|
| 6,289,334 | B1 | 9/2001 | Reiner et al. |
| 6,523,030 | B1 | 2/2003 | Horowitz |
| 6,850,925 | B2 | 2/2005 | Chaudhuri et al. |
| 6,985,898 | B1 | 1/2006 | Ripley et al. |
| 7,017,147 | B2 | 3/2006 | Hayase et al. |
| 7,137,116 | B2 * | 11/2006 | Parkes et al. ............... 718/102 |
| 7,184,967 | B1 | 2/2007 | Mital et al. |
| 7,231,390 | B2 | 6/2007 | Blair |
| 7,240,328 | B2 * | 7/2007 | Beckett et al. ............. 717/113 |
| 2002/0199034 | A1 * | 12/2002 | Beckett et al. ............. 709/328 |
| 2005/0066304 | A1 | 3/2005 | Tattrie et al. |

OTHER PUBLICATIONS

BTG Product Overview, 4 pp.

Scientific Computing Associates Inc., Paradise Product Overview, 2 pp (1995).

Paradise: User's Guide and Reference Manual, Version 6.2, Scientific Computing Associates (Apr. 2000).

"SGI Bioinformatics Performance Report," Silicon Graphics, Inc., 10 pp (Summer 2000).

Davidson et al., "Facilitating Transformations in a Human Genome Project Database," ACM, p. 423 (1994).

Yona et al., "A Unified Sequence-Structure Classification of Protein Sequences: Combining Sequence and Structure in a Map of the Protein Space", RECOM, p. 308 (2000).

Chakravarthy, "Divide and Conquer: A Basis for Augmenting a Conventional Query Optimizer with Multiple Query Processing Capabilities," IEEE, p. 482 (1991).

Jiang et al., "Dynamic Parallel Query Processing for Distributed Objects," 9th International Workgroup on Database and Expert System Applications Proceedings, p. 699 (Aug. 1998).

Salazar et al., "On An Efficient Parallelization of Exhaustive Sequence Comparison Algorithms on Message Passing Architectures," Oxford University Press, vol. 10, No. 5, p. 509 (1994).

Yap et al., "Parallel Computation in Biological Sequence Analysis," IEEE Transactions on Parallel and Distributed Systems, vol. 9, No. 3, p. 283 (Mar. 1998).

Gao et al., Multithreaded Implementation of a Biomolecular Sequence Alignment Algorithm-Software/Information Technology, IEEE, p. 494, (2000).

Wang et al., "Parallel R-Tree Search Algorithm of DSVM," Proceedings of 6th International Conference on Database System for Advanced Applications, p. 19 (Apr. 1999).

Harvey et al. The Effectiveness of Task-Level Parallelism for High-Level Vision, ACM 1990, pp. 156-167.

* cited by examiner

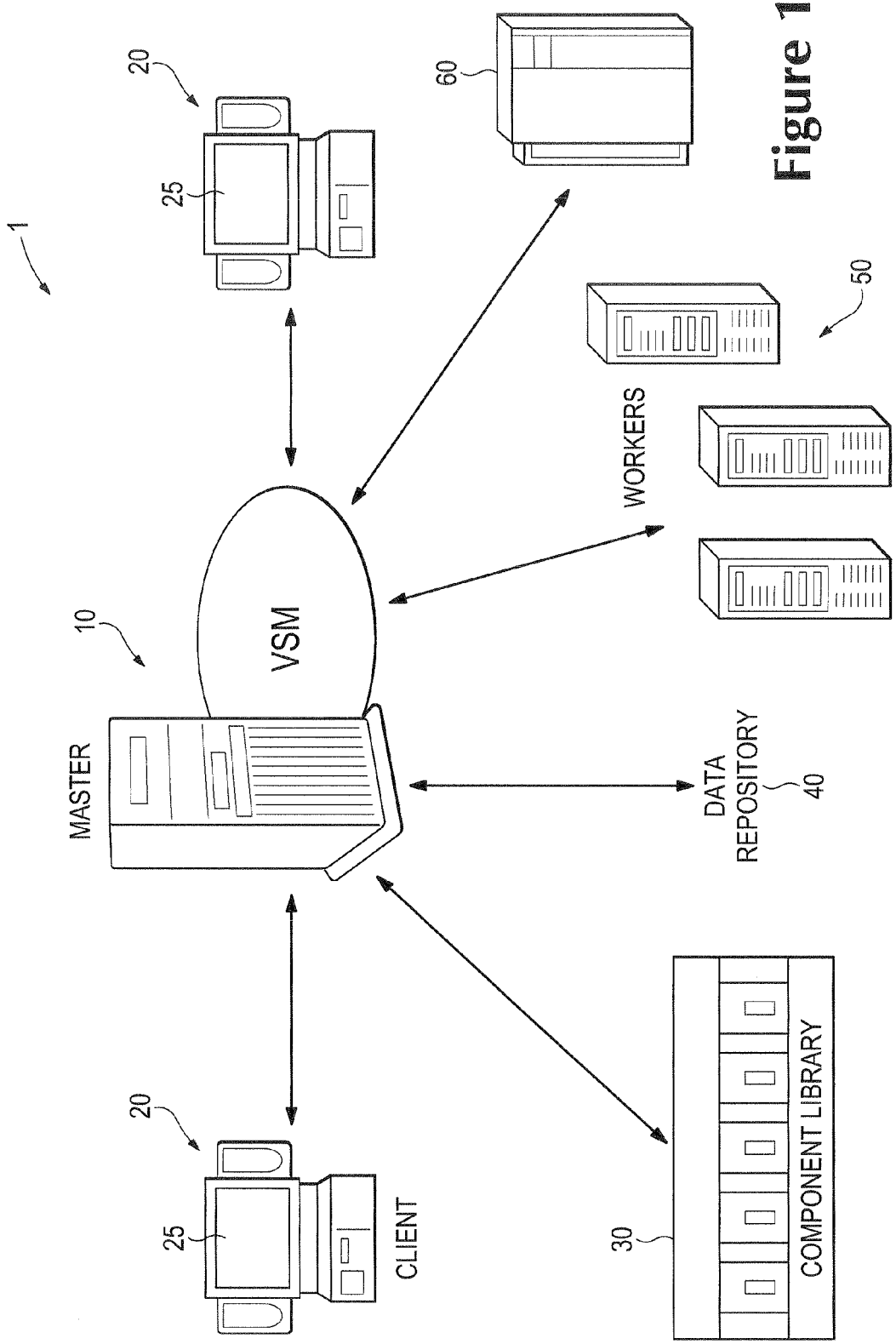

METHOD AND SYSTEM FOR DATAFLOW CREATION AND EXECUTION

This application is a continuation-in-part application Ser. No. 09/814,056 filed on Mar. 22, 2001.

FIELD OF THE INVENTION

The invention relates to methods and systems for creating and executing a computer dataflow using a graphical user interface.

BACKGROUND OF THE INVENTION

In many industries, information technology platforms for technical computing have become key differentiators and drivers of business growth. For companies in these industries—including the biotechnology, pharmaceutical, geophysical, automotive, and aerospace industries, among others—a new class of business-critical technical computing problems has arisen. These problems are complex, with solutions often involving multiple computational steps with large quantities of data passing from one step to the next. In addition, the individual computational steps themselves are often computer intensive and very time consuming.

The life science industry offers some of the best examples of this new class of applications. In pharmaceutical R&D, for example, users often query dozens of different databases using a variety of search and analysis tools, moving data from one analysis to the next in "pipelined" dataflows. These dataflows, which are both computationally intensive and logistically complex, are essential parts of the R&D process, because without them, it would be impossible to adequately investigate the large amount of data coming out of modern, highly automated laboratories.

Pipelined dataflows are also becoming part of the computing infrastructure that supports clinical medicine. Major medical centers are beginning to use complex heterogeneous databases and applications for analyzing clinical, genetic, and demographic information to make final treatment decisions. Such infrastructure is becoming a differentiator for major medical institutions.

The new class of technical computing problems described above pose a number of substantial computational challenges. First, they require huge amounts of CPU horsepower and other computational resources. For a number of years, the platforms of choice for large computations have been clusters or local-area networks of small-to-moderate-size commodity machines. Such clusters have rapidly replaced traditional large multiprocessing supercomputers for most high performance computing tasks, due largely to the substantial cost-performance advantages they offer. However, individual clusters are insufficient to meet the voracious demands of complex technical computing dataflows. This has led to a new type of high-performance computing platform based on the concept of a "computing grid" (analogous to a utility grid) made up of multiple interconnected clusters. Computing grids have a wealth of resources—CPUs, storage, communication, etc.—that may be applied to technical computations, but management of such diverse collections of resources is difficult, and effective software solutions are only now beginning to appear.

A second major challenge arises because solutions to the new class of problems must access and integrate massive amounts of data from large numbers of distinct sources. Algorithms for technical computation traditionally assume that all required data is stored locally and that the costs of data access are almost always dominated by the costs of computation. For many problems of the type considered here, however, the data may reside at numerous sites and may be stored in very diverse formats. For such problems, the costs of accessing the data and integrating it into the computational process may easily outstrip the costs of the computations themselves. This challenge is motivating the development of new data management tools capable of efficiently accessing and integrating such widely distributed data.

Finally, a third major challenge relates to the way that users manage the execution of the kind of large, complex dataflows required to solve mission-critical technical computing problems. These dataflows typically include a number of computer-intensive steps, and it is usually necessary to perform complex transformations as data is transferred between steps. Traditionally, running such dataflows has required substantial amounts of time and effort from a skilled user capable of starting and monitoring each computational step, dealing with potential processing errors, transforming the data between steps, and moving data among the different computers where computations may take place. Such a manual process is a significant impediment to the effective use of complex dataflows, since it wastes valuable time of skilled users and its tedium increases the likelihood of errors. The need to overcome such operational hurdles is driving the development of application management tools to automate and accelerate dataflow processing.

Application integration/interoperability or acceleration are essential requirements to solve this new class of technical computing problems. Application accelerators and dataflow systems are the two main tools used to address these requirements. Application accelerators are designed to improve the performance of individual, stand-alone applications. Most accelerators have evolved from a number of tools such as MPI, PVM, or Linda that were created originally to accelerate applications using special parallel programming techniques designed to exploit static sets of "worker" machines. Today, the most common application accelerators are more flexible, allowing them to exploit a set of widely distributed workers that may evolve dynamically throughout the course of a computation. However, particularly among the so-called "peer-to-peer" application accelerators touted for use on computing grids, there are often substantial tradeoffs for this flexibility that may make the accelerators unsuitable for large classes of applications. The tradeoffs include such things as limitations on file transfers to or from the worker machines, restricted or prohibited communications among the workers, constraints on the specific combinations of hardware, operating systems, and programming languages that are permitted; and restrictions or inefficiency due to security, encryption, or other requirements. In addition, in many cases, the use of application accelerators by end users may be severely limited by the fact that most of the accelerators require modification of application source code in order to deal with the transfer of data to and from the workers.

Dataflow systems take an entirely different approach to acceleration, focusing not on individual applications, but on complex pipelines of applications called dataflows that may be thought of visually as flowcharts (including logic and loops), where the flowchart boxes correspond to specific applications or data accesses. Such dataflows are common in many industries, and they are ubiquitous in the life sciences. Almost all members of the new class of mission-critical technical computing problems are, in fact, solved by dataflows, not individual applications, since the solutions require accessing data from numerous sources, applying multiple types of analysis, and making significant logistic decisions during the computational process. The key issues in dataflow systems are application integration/interoperability (including data conversion and data flow among the applications in the dataflows) and performance improvement by means of sophisticated application-specific scheduling. The best dataflow systems are able to address these issues without access to the source code of individual applications used in the dataflows; this broadens the applicability of such systems substantially as compared with the application accelerators discussed above.

Traditionally, users have applied dataflow via two approaches. The simpler one is completely manual; a user starts up the program for each step by hand, and reformats and transfers the data between steps either by hand or by using simple scripts or programs. The only real advantage of the manual method is that it is relatively easy to use and can cater to a wide variety of situations. For example, one step may require visiting a web site, filling out a form, clicking a button or two on the screen, and cutting/pasting data from the output screen into a file or the input screen for the next step. Another step may require logging into a remote machine, transferring some files, running a command-line program on the remote machine, and then transferring the result files back to the user's machine. None of this is automated, but at least the procedures are straightforward enough so that most users can perform them.

The manual approach has many drawbacks, of course. Dataflow execution is very time-consuming and error-prone, and the user must pay constant attention to ensure correct results. The traditional alternative has been to implement "automated" dataflows by writing complex scripts using a standard scripting language. Once the script is written, a user can execute the dataflow from a command line by running the script and providing whatever specific parameters and files may be required. Shell scripting languages in various operating systems are widely used for dataflow development. The Perl scripting language is a common choice for OS-independent scripts, but there are a number of others such as Python, Jython, and even Java that are more modern and may well be better choices depending on the types of data manipulations required between the computer-intensive steps of the dataflow.

Regardless of the choice of scripting language, however, script creation is effectively the same as programming. The developer uses an editor to create a dataflow script that invokes each of the computer-intensive steps as independent programs. The invocations often take place on the machine where the script executes (leading to a sequential computation), but scripting languages may make it possible (though not necessarily easy) to invoke the programs on remote machines. In between these program invocations, the developer inserts whatever code is required to handle errors that might arise, perform the data manipulations required to convert the data from the output format of one step to the input format of the next, and move data around among multiple machines (if different steps run on different machines). The data operations themselves may be coded in the scripting language, or they may be implemented by invoking a separate program to filter the data in some way, but they are rarely designed to be reused in other dataflows. Correct dataflow operation is entirely the responsibility of the developer, and it is unusual to encounter dataflow scripts that operate correctly in more than a few environments that happened to be important to the developer when the dataflow was created.

SUMMARY OF THE INVENTION

The present invention is directed to a method for creating and executing a computer dataflow using a graphical user interface. A plurality of components is defined, based on an input, an output, metadata and a sub-interpreter, where each of said components represents a computer-implemented computational process that is performed on one or more inputs to the component. The computer-implemented computational process generates one or more outputs based on a predefined computational algorithm. The user is provided with a graphical user interface that allows the user to visually create the computer dataflow on a user display. The user selects components, from a library of components, and graphically connects one or more input terminals of selected components with one or more output terminals of second selected components. Each selected component and the one or more input terminals graphically correspond to the one or more inputs to the predefined computational algorithm associated with the component. The one or more output terminals graphically correspond to the one or more outputs generated by the predefined computational algorithm associated with the component. Without the user's intervention, at least one of said selected components is distributed for execution across a plurality of machines during performance of the computer dataflow. The component automatically executes upon receiving a minimum number of inputs. The present invention also includes an apparatus and tangible medium that accomplish this method.

The invention is also directed to a method for creating and executing a computer dataflow using a graphical user interface. A plurality of components is defined, based on an input, an output, metadata and a sub-interpreter, where each of the components represents a computer-implemented computational process that is performed on one or more inputs to the component. The computer-implemented computational process generates one or more outputs based on a predefined computational algorithm. The user is provided with a graphical user interface that allows the user to visually create the computer dataflow on a user display. The user selects components, from a library of components, and graphically connects one or more input terminals of selected components with one or more output terminals of second selected components. Each selected component and the one or more input terminals graphically correspond to the one or more inputs to the predefined computational algorithm associated with the component. The one or more output terminals graphically correspond to the one or more outputs generated by the predefined computational algorithm associated with the component. For at least one selected component, the graphical user interface allows the user to conditionally designate output of the predefined computational algorithm which satisfies at least one condition to a first output terminal. The graphical user interface also allows the user to conditionally designate the output of the predefined computational algorithm, which fails to satisfy the at least one condition, to a second input terminal. The present invention also includes an apparatus and tangible medium that accomplish this method.

The invention is further directed to a method for executing a computer dataflow during which a plurality of master entities submit tasks to be performed, and a plurality of worker entities perform tasks submitted by the master entities. A taskbag abstraction layer is defined that interacts between the master entities and the worker entities. Scheduling logic for selecting which worker should perform a given task is coded in the taskbag abstraction layer. Additionally, communication logic is also coded in the taskbag abstraction layer where the logic indicates how results should be transmitted between a worker entity and a master entity associated with the given task. During execution of the dataflow, a master entity submits a task to the taskbag abstraction layer without providing information to the taskbag abstraction layer indicating how to schedule the submitted task or transmit results of the submitted task. During execution of the dataflow, a worker entity retrieves a task from the taskbag abstraction layer without retrieving from the taskbag abstraction layer information indicating how to schedule the retrieved task or transmit results of the retrieved task. The present invention also includes an apparatus and tangible medium that accomplish this method.

The invention is further directed to a method for executing a computer dataflow that accesses and stores data to and from a plurality of different systems. Each of the different systems uses a different mechanism for accessing and storing data. A data repository abstraction layer is defined that is used by the computer dataflow. The abstraction layer provides a uniform naming format for each of the different mechanisms for accessing and storing data. The uniform naming format includes a first field representing an object type and a second field representing an object location. During creation of the computer dataflow, data object references are defined by a graphical user interface wherein each data object reference has an object type representing a data format and an object location representing a physical location. During execution of the computer dataflow, each data object in the dataflow is interpreted, where the data object is represented in accordance with the uniform naming format. Based on the interpretation, a generic constructor delegates, either an access or storage process associated with the data object, to a subconstructor that corresponds to the object type of the data object. The present invention also includes an apparatus and tangible medium that accomplish this method.

The invention is directed to a method for executing a computer dataflow that accesses and stores data to and from a plurality of different systems. Each of the different systems uses a different representation of data and optionally a different mechanism for accessing and storing data. A plurality of components is defined where each of the components represents a computer-implemented computational process. The process is performed on one or more inputs to the component and generates one or more outputs based on a predefined computational algorithm. A uniform description format is defined for each of the different representations of data and the different mechanisms for accessing and storing data. The uniform description format includes a field representing data type. A graphical user interface is provided that allows a user to visually create the computer dataflow on a user display by selecting from a library of the components, and graphically connecting one or more input terminals of selected components with one or more output terminals of second selected components. For each selected component, the one or more input terminals graphically corresponds to the one or more inputs to the predefined computational algorithm associated with the component, and the one or more output terminals graphically correspond to the one or more outputs generated by the predefined computational algorithm associated with the component. If one or more inputs of a selected component has a data type that does not match one or more outputs of the selected component, the graphical user interface determines whether a corresponding converter exists. If a corresponding converter does not exist, the graphical user interface prompts the user to perform a data mapping between at least one input data type and at least one output data type at creation of the computer dataflow. The present invention also includes an apparatus and tangible medium that accomplish this method.

The invention is further directed to a method for creating and executing a computer dataflow. A plurality of components is defined based on an input, an output, metadata and a sub-interpreter. Each of the components represents a computer-implemented computational process. The process is performed on one or more inputs to the component and generates one or more outputs based on a predefined computational algorithm. A graphical user interface is provided that allows a user to visually create the computer dataflow on a user display by selecting from a library of said components, and graphically connecting one or more input terminals of selected components with one or more output terminals of second selected components. For each selected component, there is one or more input terminals that graphically correspond to the one or more inputs to the predefined computational algorithm associated with the component, and the one or more output terminals graphically correspond to the one or more outputs generated by the predefined computational algorithm associated with the component. A component interpreter abstraction layer is defined that facilitates execution of a component by examining a name of the component, the one or more inputs and the one or more outputs associated with the component. The layer then selects and invokes a sub-interpreter based on the name of the component, the one or more inputs and the one or more outputs associated with the component. Without intervention from the user, the plurality of said selected components is distributed across a plurality of machines during performance of the computer dataflow for execution, wherein the component automatically executes upon receiving a minimum number of inputs. The sub-interpreter executes the component using the input, output and metadata. The present invention also includes an apparatus and tangible medium that accomplish this method.

BRIEF DESCRIPTION OF THE DRAWINGS

The accompanying drawings, which are included to provide further understanding of the invention and are incorporated in and constitute a part of this specification, illustrate embodiments of the invention and, together with the description, serve to explain the principles of the invention.

In the drawings:

FIG. 1 illustrates a system used in connection with the present invention.

DETAILED DESCRIPTION OF THE PREFERRED EMBODIMENTS

Figure 2A:
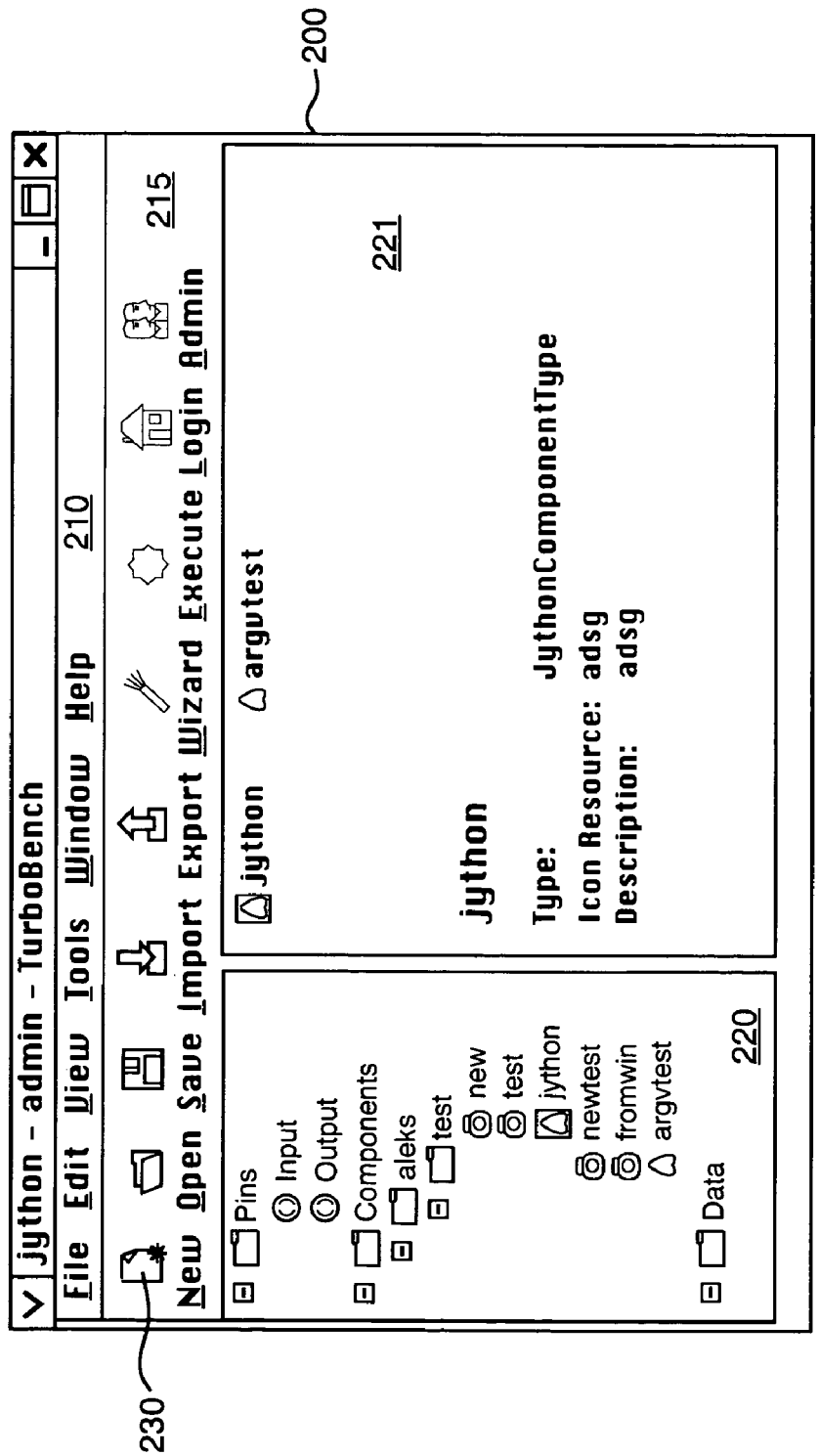
FIGS. 2A through 2M illustrate an exemplary graphical user interface that may be used for creating a command line component in connection with the present invention.

FIG. 1 illustrates system 1 that may be used to carry out the methods of the present invention. System 1 includes master computer 10, user computer(s) 20, graphical user interface (GUI) 25, component library 30, data repository 40, worker computer(s) 50, and virtual shared memory (VSM) 60. The master computer 10 includes a master program which accepts job requests from the user computer(s) 20, posts tasks in VSM 60, and temporarily stores completed task results until the entire job is finished. Worker computer(s) 50 retrieve data and tasks and execute the computational portions of dataflows. The number of worker computer(s) 50 may change at any time and may include a wide range of different types of computers running any standard operating system. GUI 25 runs on each user's desktop machine, enabling users to create and execute components and dataflows. The component library 30 is a shared database that stores information about the programs, components and dataflows in system 1. Multiple copies of components are stored in the component library 30 and these components are downloaded from the component library 30 when the worker computer(s) 50 pick up tasks from a central task list. The data repository 40 is a network storage facility that stores data (or, in some cases, information that makes it possible to find and access data stored elsewhere) and provides a standardized place to find input data or store results. VSM 60 is a shared object repository for controlling the execution of tasks and storing the results.

The components stored in the component library 30 consist of executable programs or scripts, along with some descriptive information (known as metadata). Each component includes four arguments: input and output arguments, metadata and the executable itself. The executable portion of a component typically runs a computational algorithm or retrieves data from a database or other data source. The component's metadata may be written in any parseable form describing the component's inputs and outputs and its data files. It also describes the component's sub-interpreter that should be invoked for the component invocation. It may optionally include information such as the type of object methods for a java component and how to construct a command line for a compiled executable sub-interpreter. Components may be readily shared, modified, debugged, and reused. Tables 1 and 2 illustrate XML for a java Adder component and a command line component that invokes a Perl script, respectively.

TABLE 1

```
version="1.0" encoding="UTF-8"?>
<component
type=
"com.turbogenomics.turbohub.component.java.JavaComponentType">
   <description>Integer Addition</description>
   <schedulerGroup/>
   <dependencies/>
   <inputs>
      <pin name="i0" javatype="int"/>
      <pin name="i1" javatype="int"/>
   </inputs>
   <outputs>
      <pin name="out" javatype="int"/>
   </outputs>
   <content>
      <java>
         <execMethod>add</execMethod>
         <className>com.turbogenomics.turbohub.components.Adder
         </className>
```

TABLE 1-continued

```
         <inputMethod name="i0">setIn0</inputMethod>
         <inputMethod name="i1">setI1</inputMethod>
         <outputMethod name="out">getResult</outputMethod>
      </java>
   </content>
</component>
<?xml version="1.0" encoding="UTF-8"?>
```

TABLE 2

```
<component
type=
"com.turbogenomics.turbohub.component.cli.CliComponentType">
   <description>Hello Perl</description>
   <schedulerGroup/>
   <dependencies/>
   <inputs>
      <pin name="in" javatype="java.lang.String"/>
   </inputs>
   <outputs>
      <pin name="out" javatype="java.lang.String"/>
      <pin name="err" javatype="java.lang.String"/>
   </outputs>
   <content>
      <files>
         <file id="in">
            <contents><inputValue name="in"/></contents>
         </file>
         <file id="_out" copyto="out"/>
         <file id="_err" copyto="err"/>
         <file id="s">
            <contents><resource name="script"/></contents>
            <!-- If you want to specify script name
            <child>hello.pl</child>-->
         </file>
      </files>
      <cli>
         <executable>perl</executable>
         <args>
            <arg><filePath ref="s"/></arg>
            <arg><filePath ref="in"/></arg>
         </args>
      <cli>
   </content>
</component>
```

Each component is executed by passing its definition to a generic interpreter. This interpreter determines the type of component, and the appropriate subinterpreter that will actually execute the component. The interpreter creates an instance of the correct subinterpreter and passes execution of the component to that subinterpreter, as illustrated in lines 1-2 of Table 2. The subinterpreter reads the rest of the component definition, which is customized to the needs of this particular type of component. The subinterpreter handles the inputs, creates the execution environment, and actually runs the component. It gathers the outputs, and passes them back to the generic interpreter, which forwards the outputs to their destination. Table 3 illustrates pseudo-code for a component sub-interpreter.

TABLE 3

```
Interpreter(component def) {read component def, determine appropriate
subinterpreter
 Interpreter i = create subinterpreter
 i.instantiate(component def)
 outputs = i.invoke(component def, inputs)
 pass outputs to destination}
```

System 1 may include pre-built application components and user created components. The pre-built application components may include components for such common tasks as displaying results in html for viewing in a web browser, or storing various types of computational results to data repository 40. It may also include components used to solve computations in biotechnology, pharmaceutical, geophysical, engineering, chemistry, automotive, aerospace, or finance disciplines. Examples include programs such as FORMATDB, BLASTALL (and other members of the BLAST suite of programs such as BLASTP), CLUSTALW, HMMBUILD, HMMCALIBRATE, HMMSEARCH, FLUENT, PTRAN AND GAUSSIAN.

The user created components are created via GUI 25. During the component creation process, the user defines the component's resources, inputs, outputs and executable files. Using GUI 25, the user may create four types of components: command line components; java components; jython components; and dataflow components. A command line component is a component that wraps a command. It describes the files needed for the proper running of an executable, the environment needed by the executable, and the exact form of the command line required by the executable. It is created after creating the original executable. Any of the parts (files, environment, command line) may be based on constant values, input values, property values, or values from a global map. In addition, the files may include data from resource files that were submitted when the component was sent to the component library 30. A Jython component wraps Jython code with the input and output pins accessed through Jython variables. It consists of a set of python scripts, one of which is the main script, executed as the component. Java components wrap Java classes, invoke methods on that class, and use the get and set methods for the inputs and outputs. A dataflow component includes more than one component whereas a command line component, a java component and a jython component exist independently of a dataflow component.

Figure 2B:
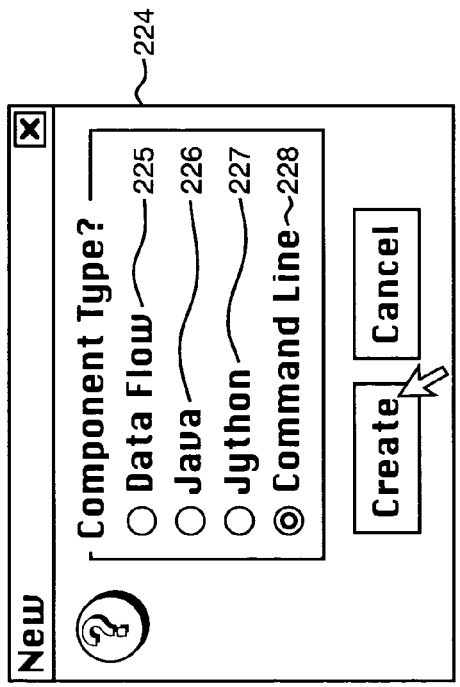
Figure 2C:
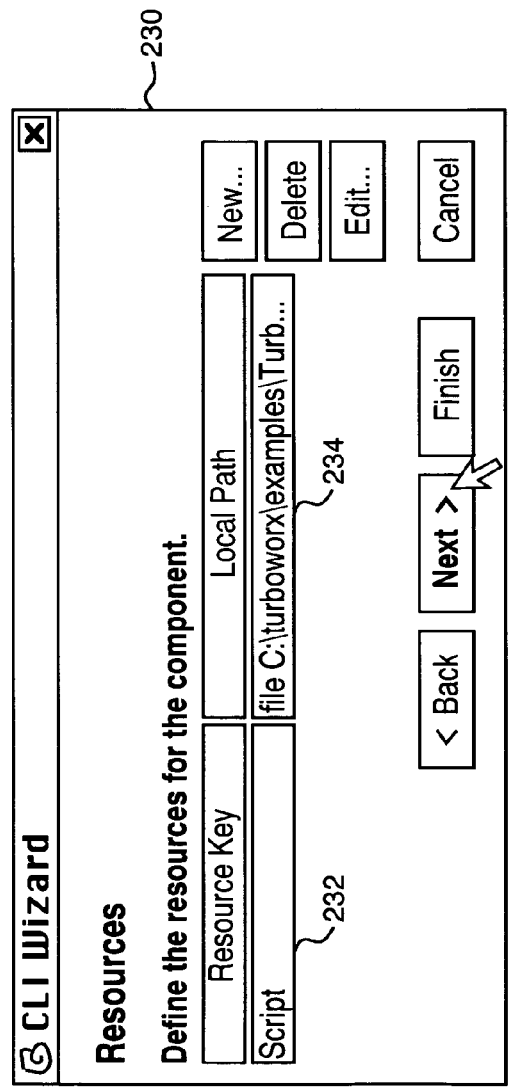
Figure 2D:
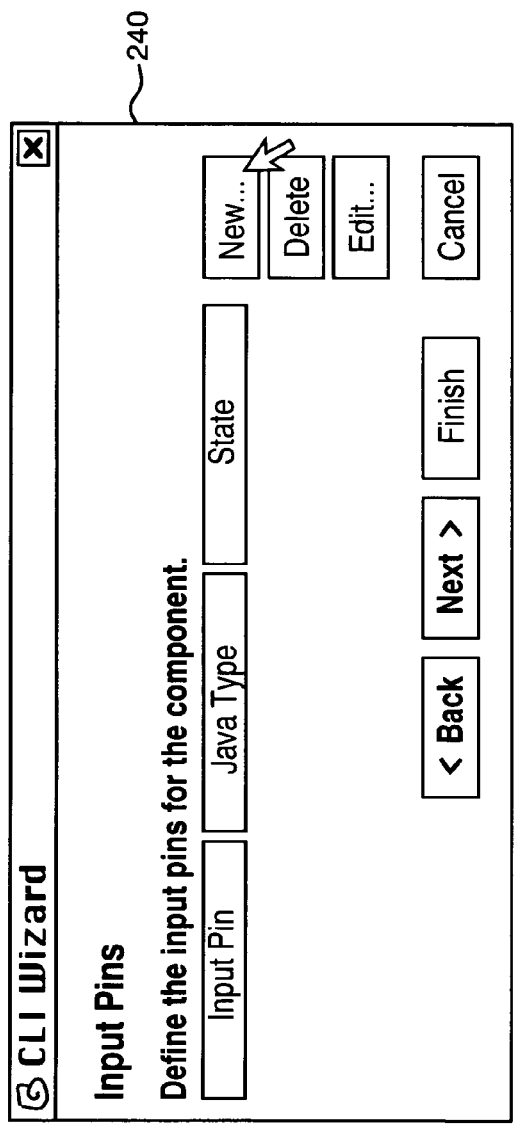
Figure 2E:
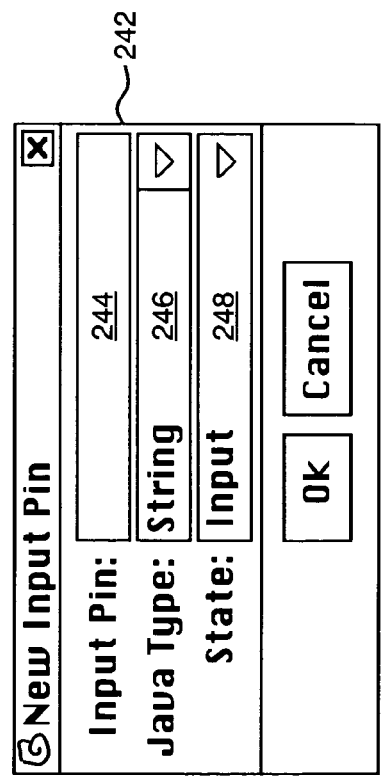
Figure 2F:
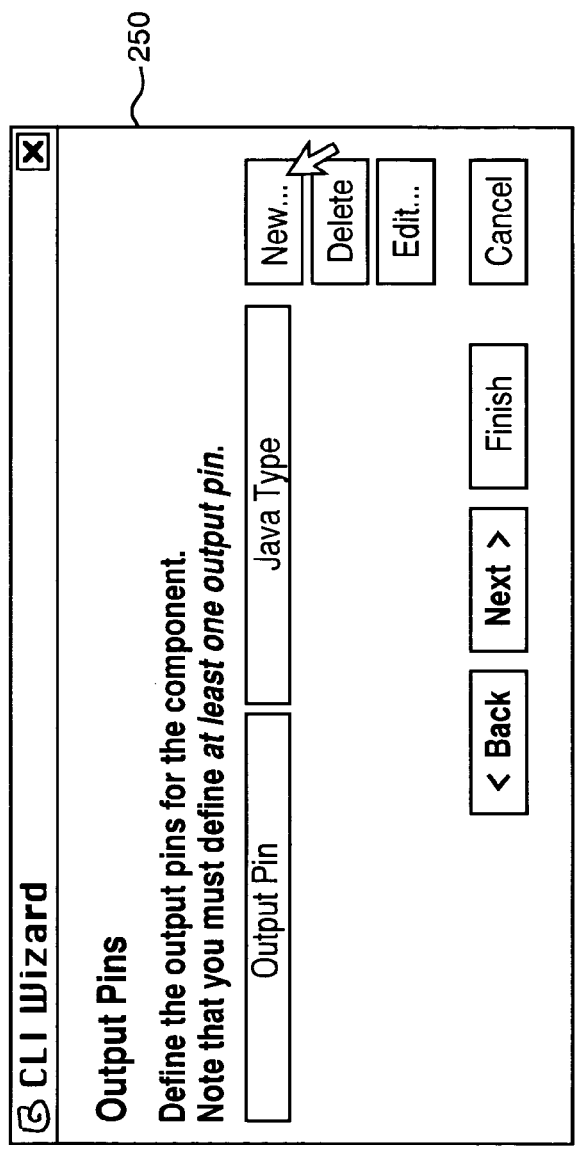
Figure 2G:
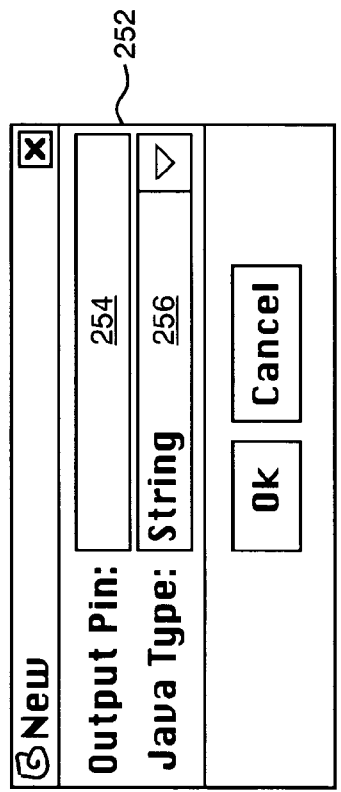

The creation of an exemplary command line component is illustrated in FIGS. 2A-2M. The main screen 200 of GUI 25 contains a button bar 215, a menu bar 210, a left panel 220 and right panel 221. The left panel 220 is used for displaying input and output pins and the library of pre-built and user-created components. Right panel 221 is used to create components and dataflow components. To create a component, the user first clicks the new button 230, on screen 200, to display the component type screen 224, FIG. 2B. After selecting the command line type 228 the user must define the component's resource file name 232 and path 234 as in screen 230, FIG. 2C. Resources are files associated and stored with the component definition. These resources vary depending on the executable or script used to create the component. As shown in FIG. 2D, the user then defines the input pins, using screen 240, which are data retrieved from VMS 60. The data is supplied to VMS 60 by the component, other components, the user, or the data repository 40. The input pin is then assigned a name 244, the java type 246 and state 248 in screen 242, as shown in FIG. 2E. The user then creates an output pin, screen 250, by assigning a name 254 and identifying the java type 256 in screen 252, FIGS. 2F and 2G.

Figure 2H:
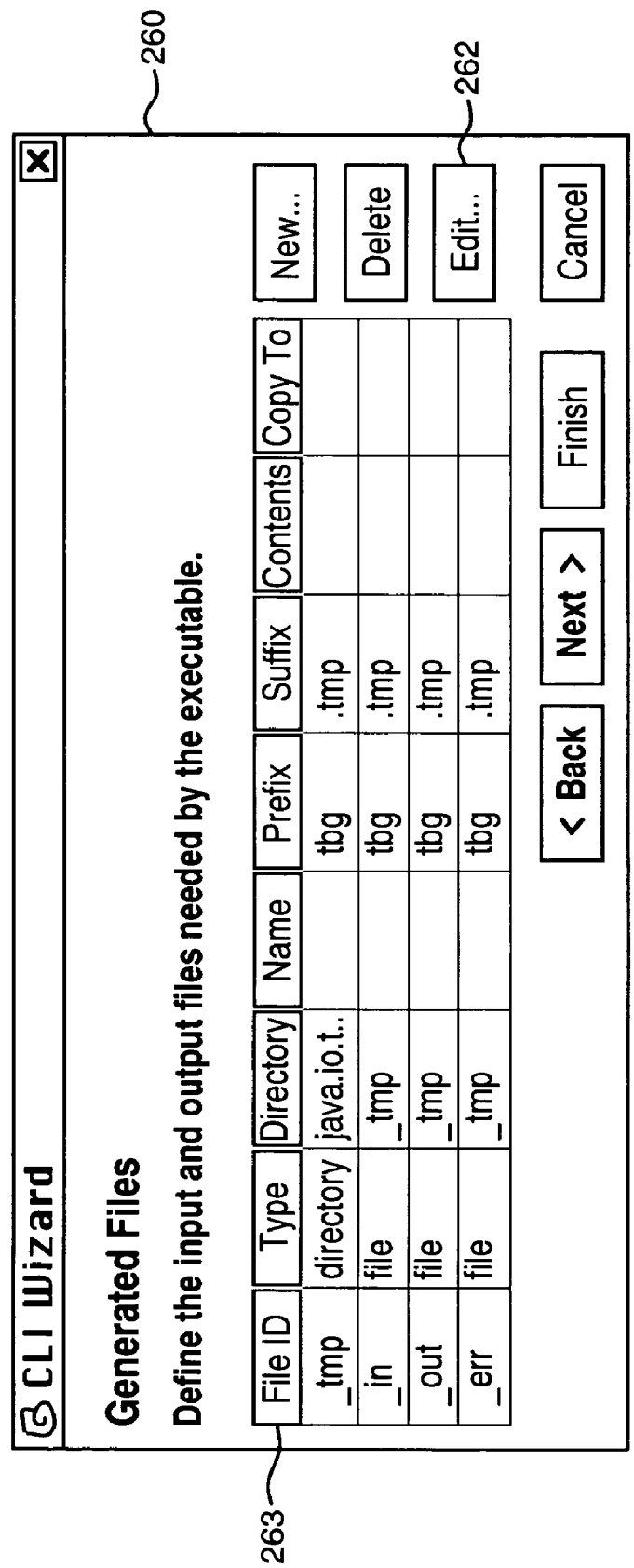
Figure 2J:
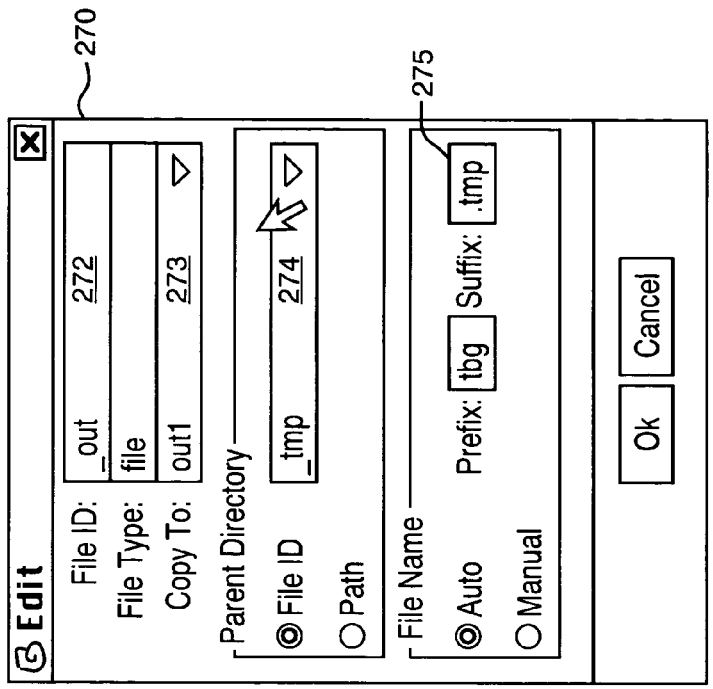
Figure 2I:
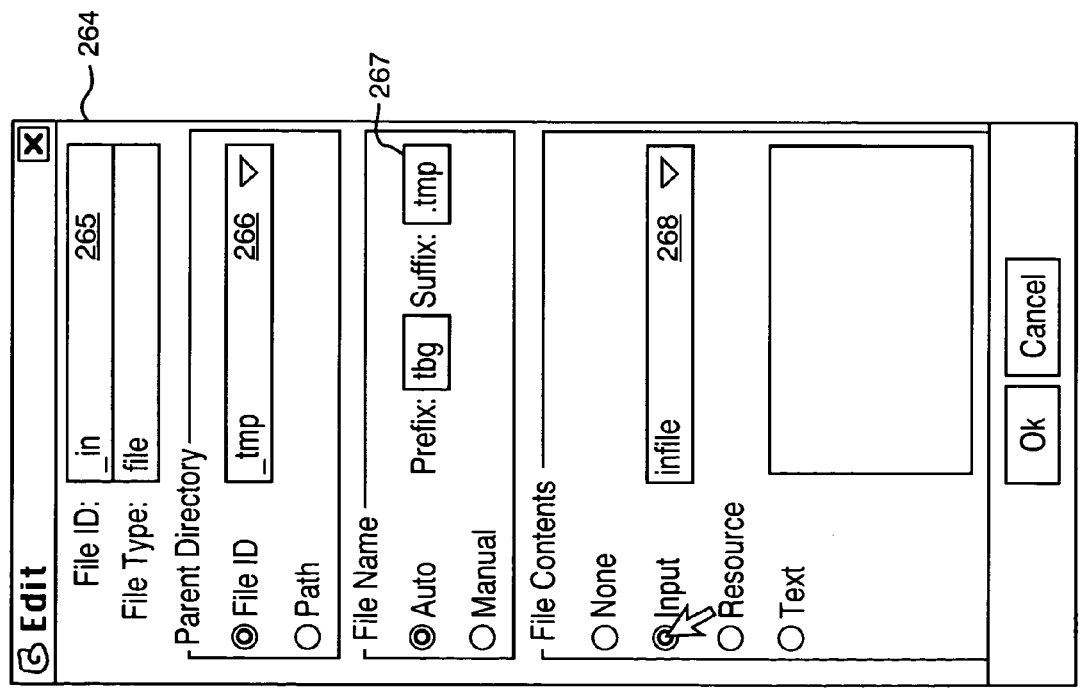
Figure 2K:
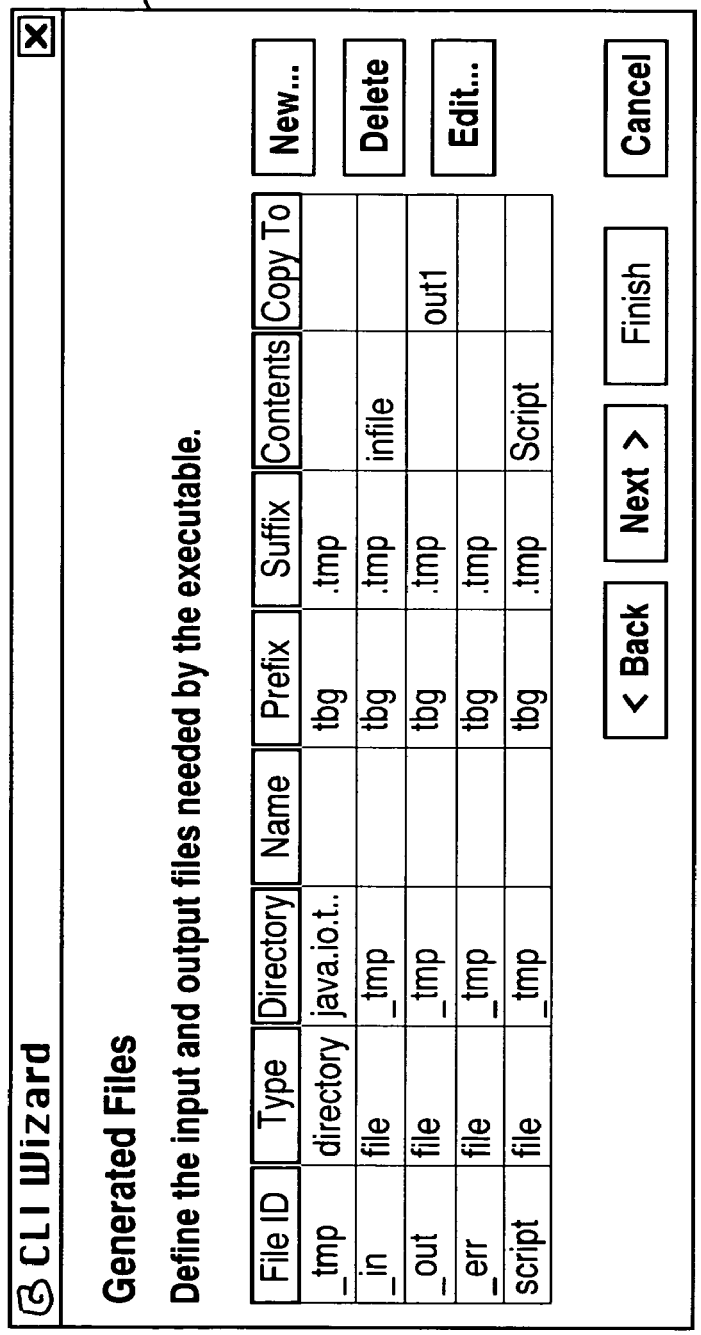

When the input(s) of the selected component has a data type that does not match the output(s) of the selected component, the GUI 25 determines whether or not a corresponding data converter exists. If a corresponding data converter does not exist, the GUI 25 prompts the user to perform a data mapping between the input data type and the output data type. To map the input, the user highlights _in from the file ID column 263 and then clicks the edit button 262 of the generated files screen 260 to map the data input as illustrated in FIG. 2H. The edit file dialog screen 264 appears and the user must click the input option 268 and enter the default values for the parent directory 266 and the file name 267 entries, FIG. 2I. To map the data output, the user highlights _out from the file ID column 263 and then clicks the edit button 262 of the generated files screen 260, FIG. 2J. The user then chooses the output option in the copy to entry 273, specifies where to send the results in entry 274 and enters the suffix of the result file name 275 in the edit file dialog screen 270, FIG. 2J. The generated files screen 278 is shown in FIG. 2K.

Figure 2L:
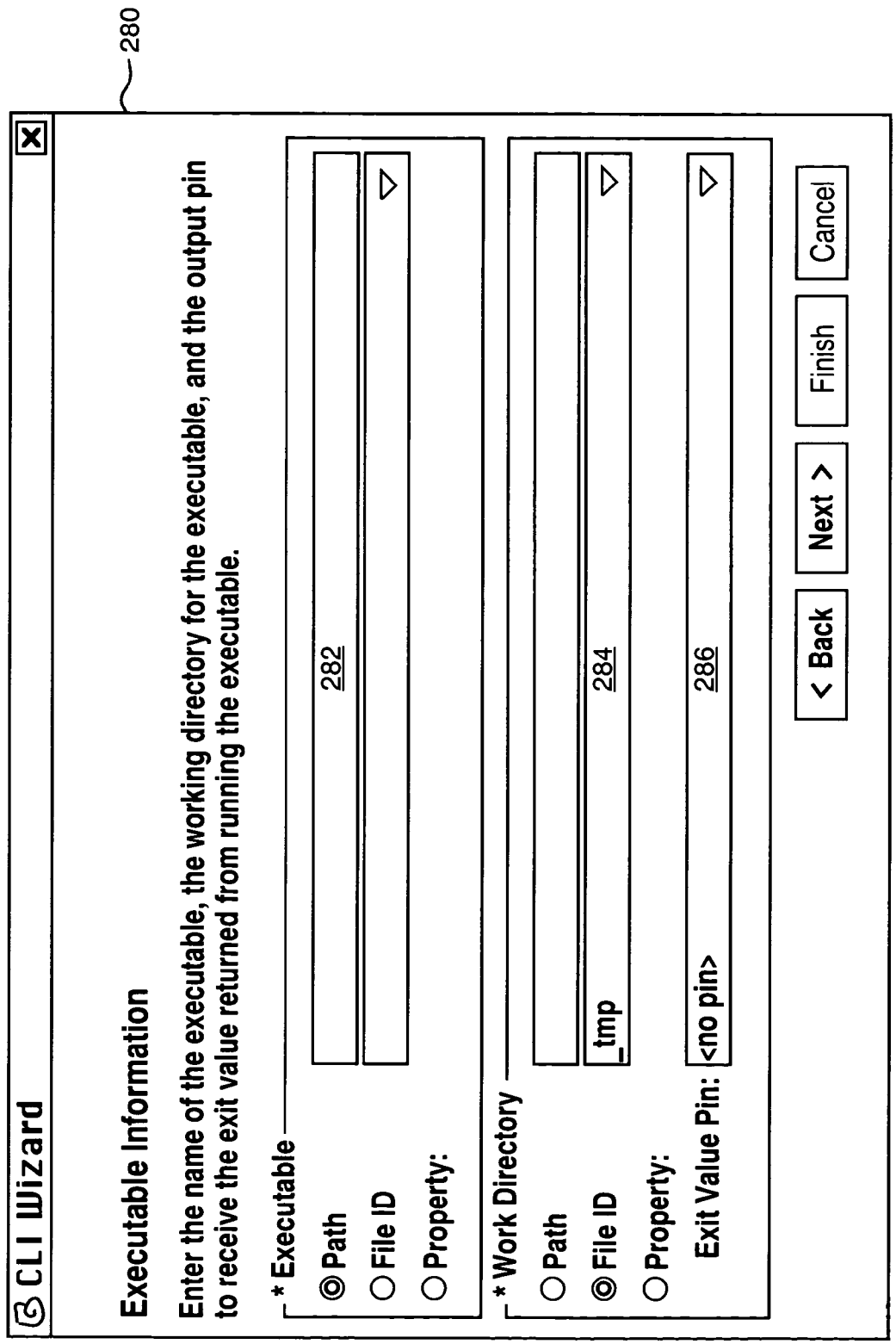
Figure 2M:
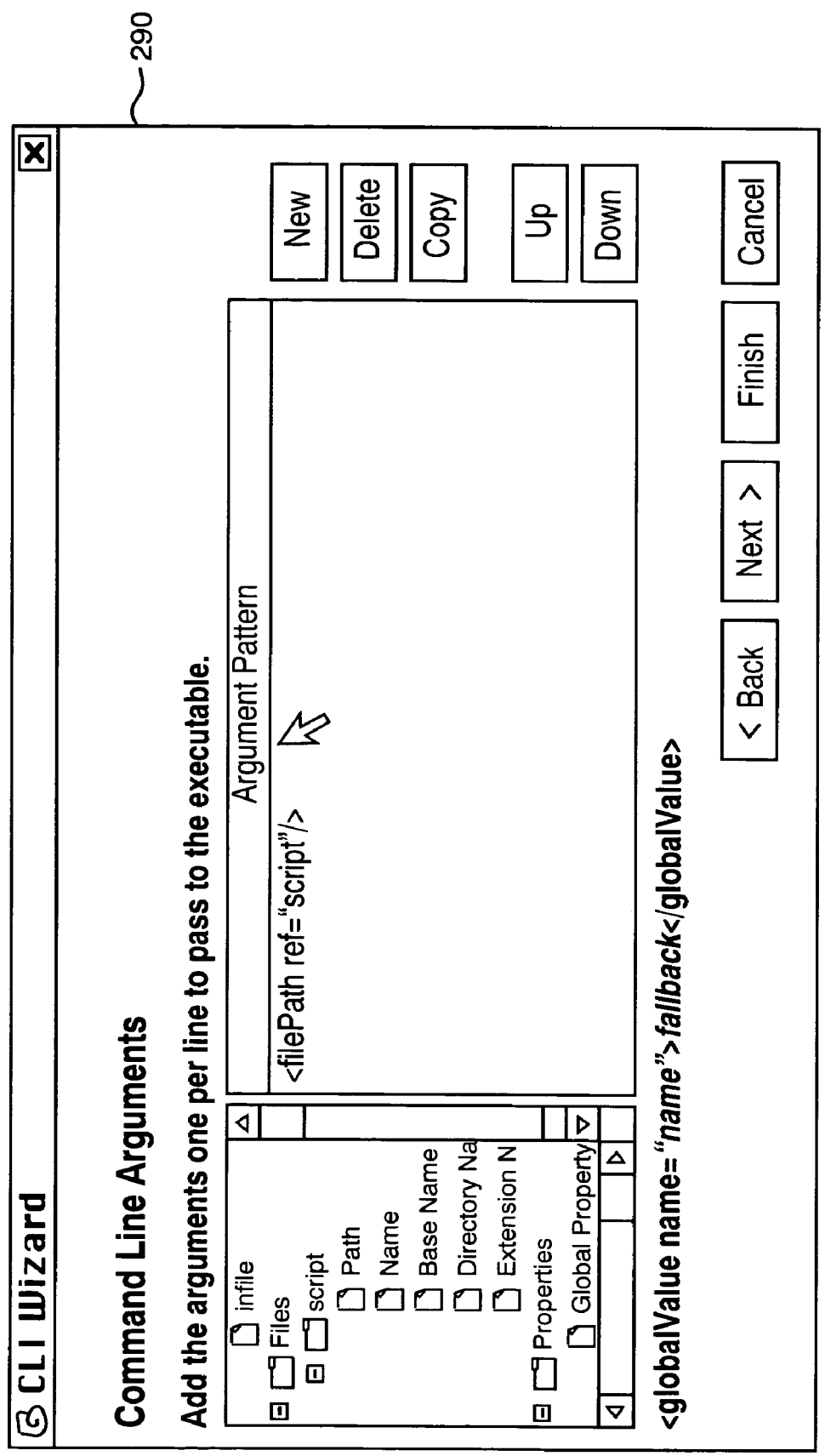

Lastly, the user also enters the executable name 282, the working directory 284 and the exit value pin 286 for the executable via screen 280, FIG. 2L. The work direction option allows the user to specify the temporary place where all the executable task are performed. The command line argument screen 290, FIG. 2M, allows the user to add an argument.

Figure 3A:
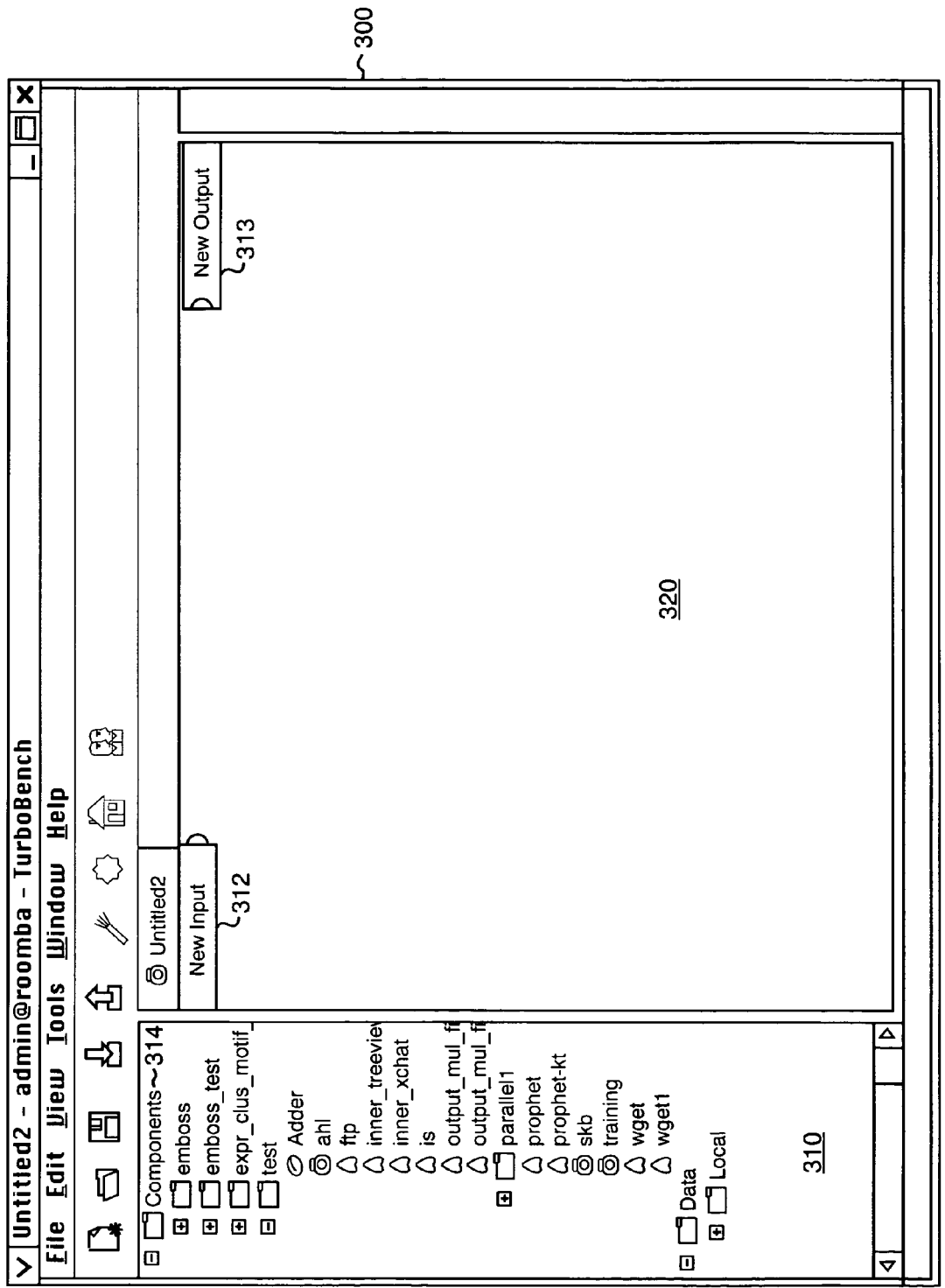
FIGS. 3A through 3F illustrate an exemplary graphical user interface that may be used for creating a dataflow component in connection with the present invention.
Figure 3B:
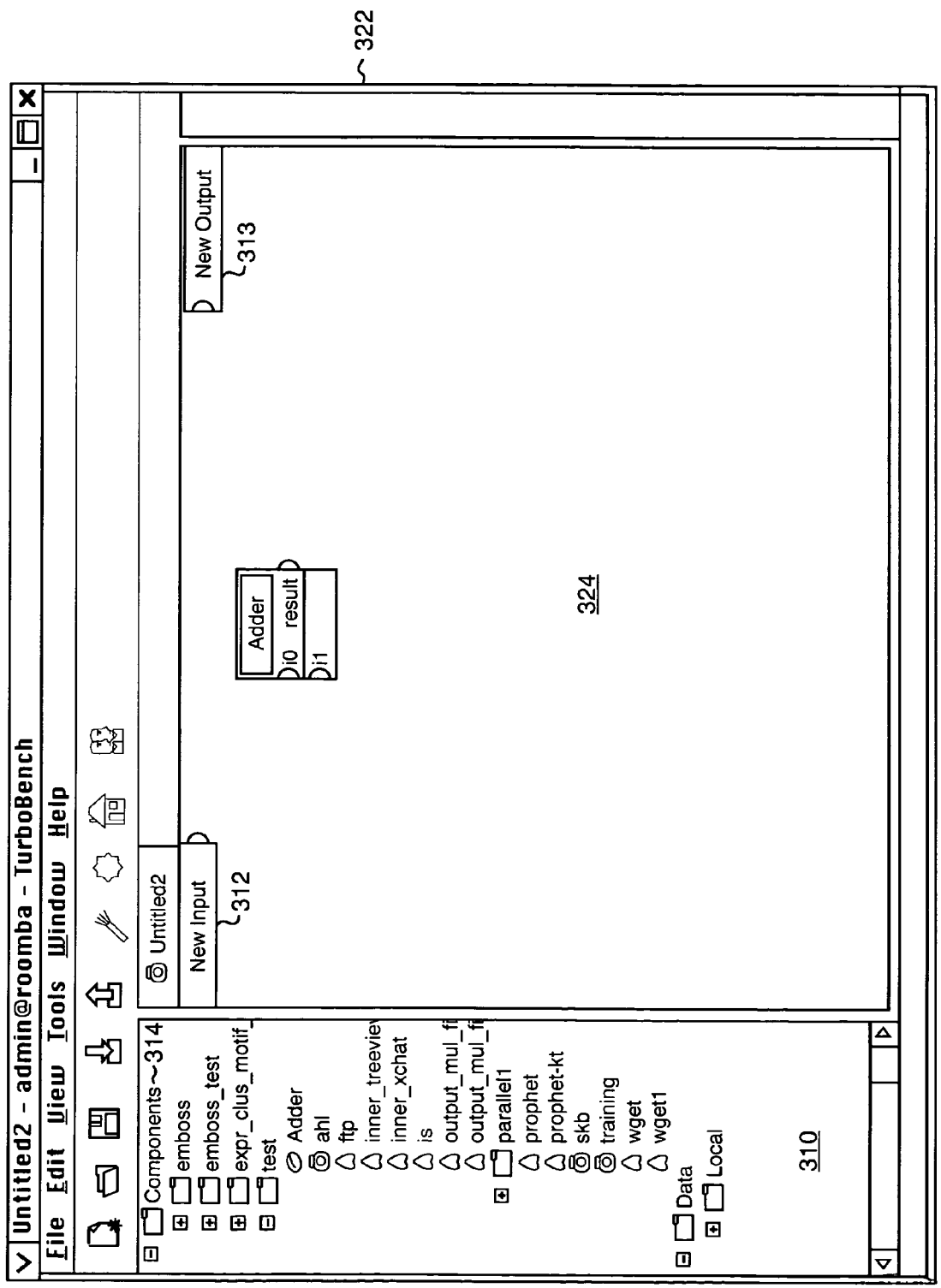
Figure 3C:
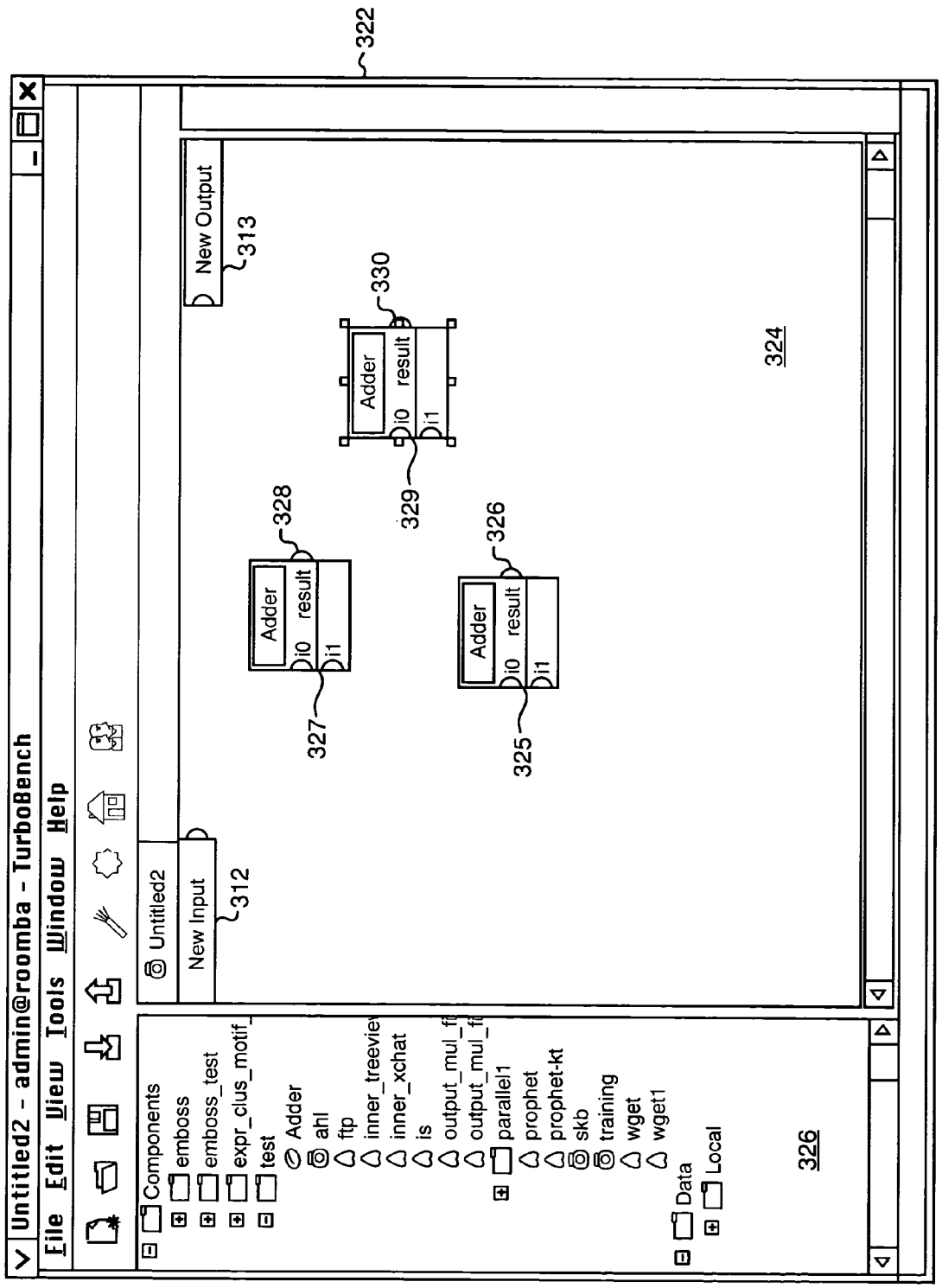
Figure 3D:
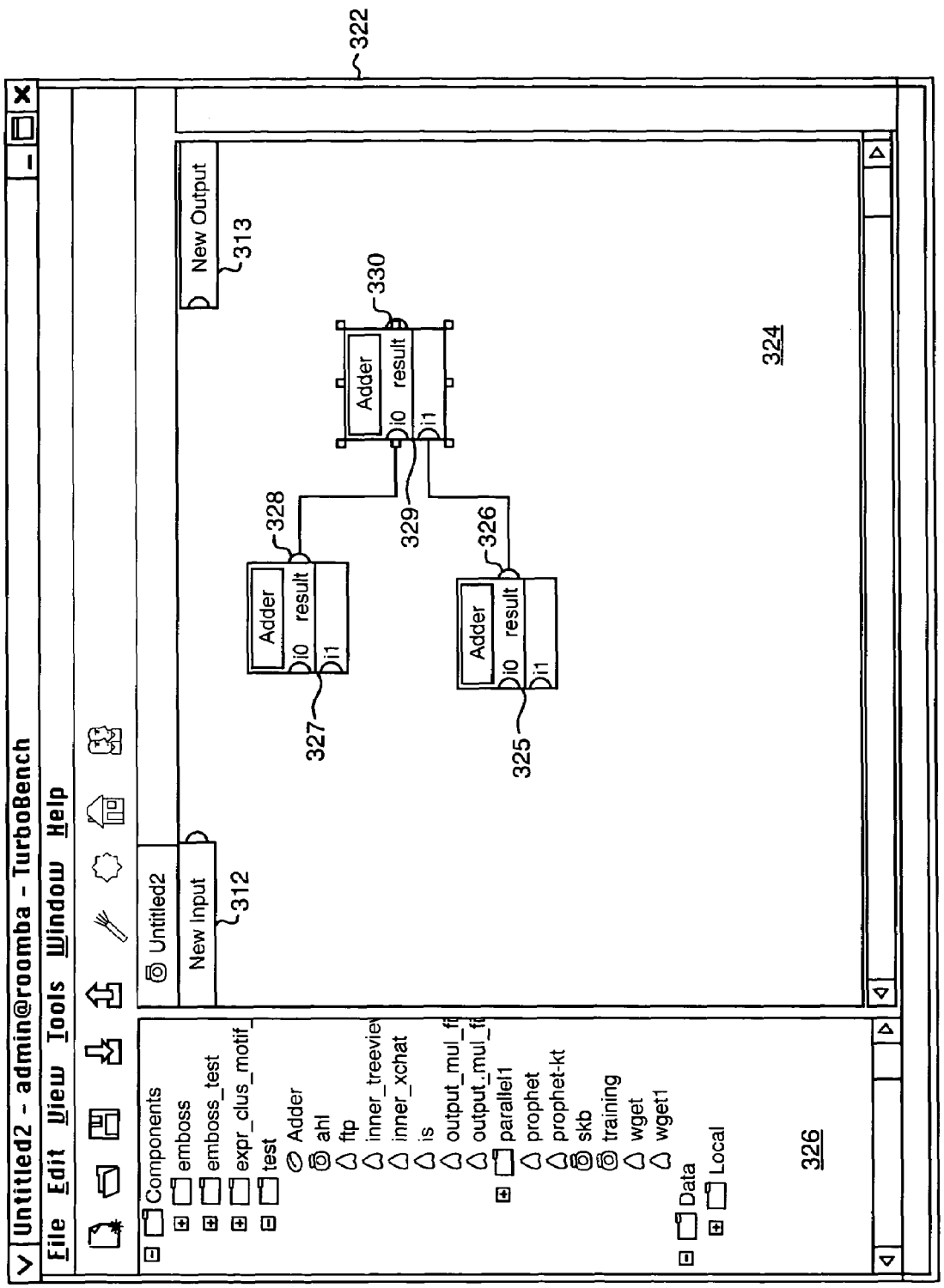
Figure 3E:
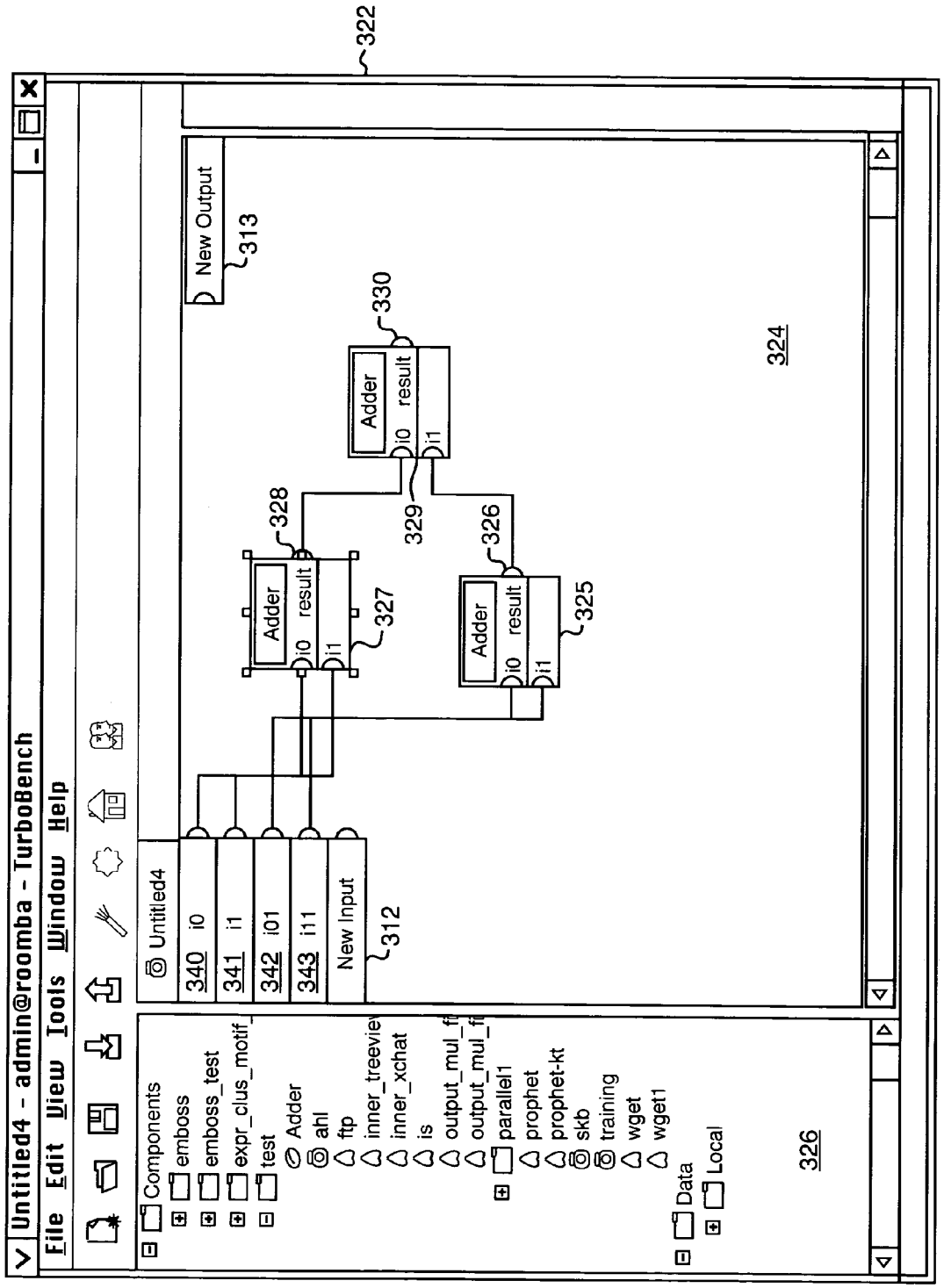
Figure 3F:
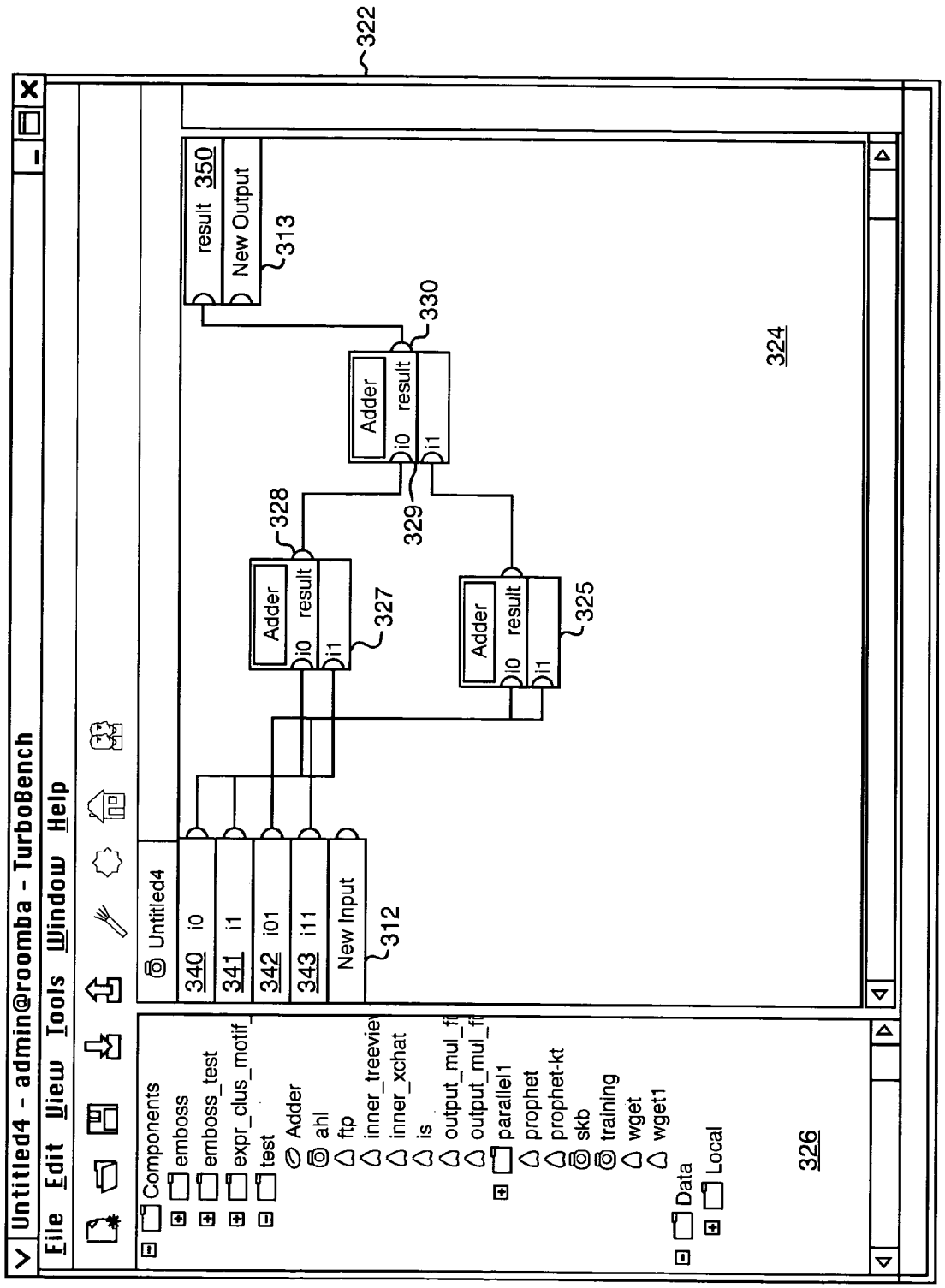

GUI 25 is also used to create a dataflow where each compute-intensive step in a dataflow is embodied in a component. GUI 25 allows the user to click and drag pre-built or user created components and input/output icons from left panel 220 to right panel 221 to create a dataflow. The creation of an exemplary dataflow is illustrated in FIGS. 2A-2B and 3A-3F using Adder components. An Adder component is used to add two numbers. As shown in FIGS. 2A and 2B, the user first clicks the new button 230 on screen 200 to display the component type screen 224, to create a dataflow. The user then selects the dataflow option 225. The dataflow component screen 300 then appears, FIG. 3A. The user may then click and drag the required components 314 from the component library of the left panel 310 to the right panel 324, FIGS. 3B and 3C. FIG. 3C illustrates a dataflow creation with three Adder components displayed in the dataflow creation screen 324 where each Adder component has two component inputs 325, 327, 329 and one component result 326, 328, 330. To connect the component result 326, 328, 330 with the input of other components 325, 327, 329, the user clicks the result 328, 326 of one of the Adder icons and then clicks the input 329 of a different Adder icon as shown in FIG. 3D. The user then connects the inputs 325, 327 of the remaining Adder components to input pins 340, 341, 342, 343, FIG. 3E. Lastly, the user connects the result 330 of the Adder component to result pin 350. The completed dataflow is illustrated in FIG. 3F.

Figure 4:
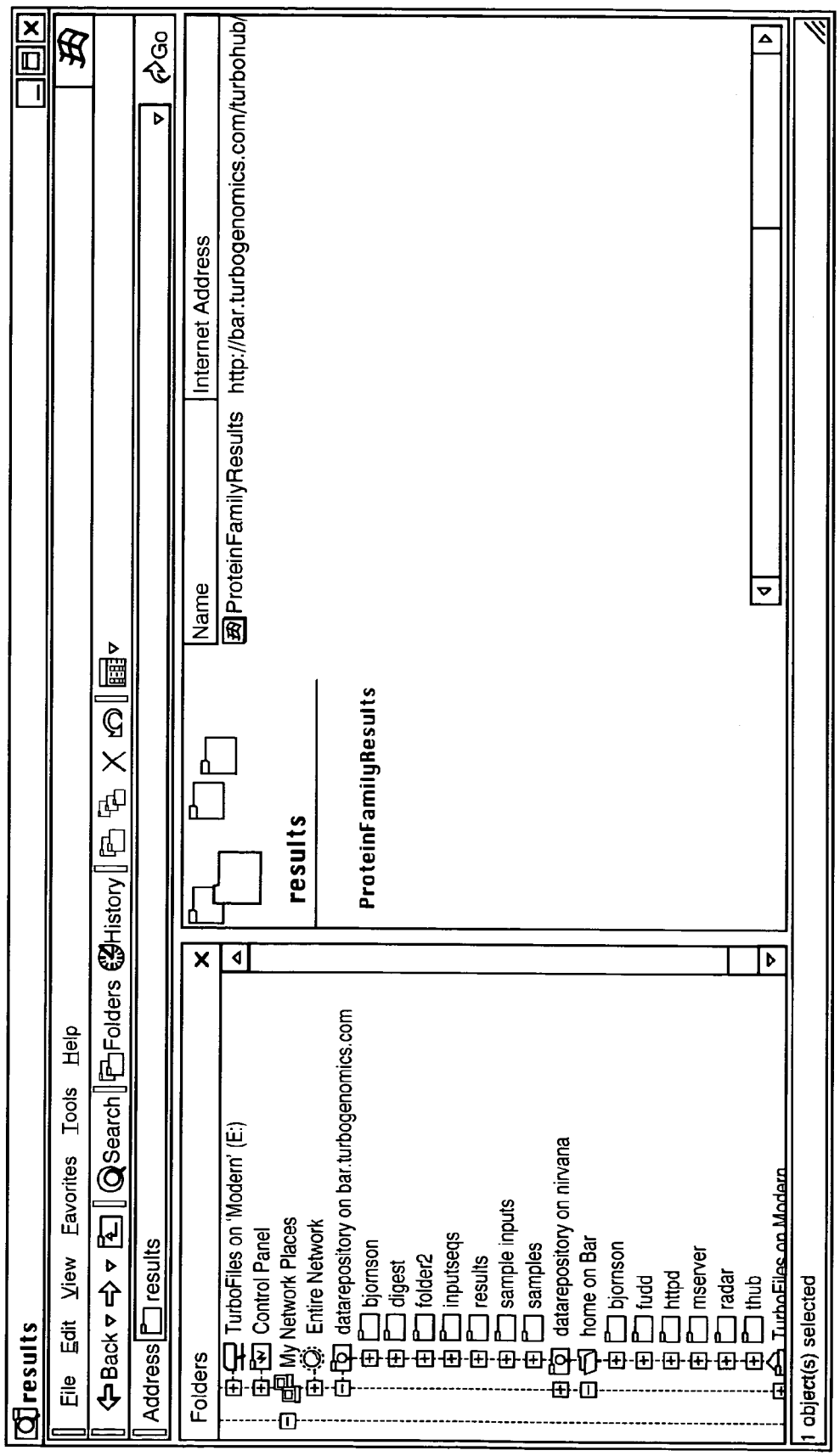
FIG. 4 illustrates an exemplary graphical user interface that may be used to input data into a data repository in connection with the present invention.

Data repository 40 functions to access and store data for components and dataflows. The data may be distributed across a plurality of systems and stored remotely from the worker 50 and master 10 computers. Data is installed in and accessed from the data repository 40 using a graphical interface such as Windows Explorer, GUI 25, WebDAV interface or other browsers. An exemplary graphical interface is illustrated in FIG. 4.

The data repository 40 may include a plurality of data storage systems. Exemplary systems include data repository on bar.turbogenomics.com and data repository on nirvana, as illustrated in FIG. 4. The plurality of systems, within data repository 40, may use different representations of data and different mechanisms for accessing and storing data. The method of the present invention provides a data repository abstraction layer. The abstraction layer allows for uniform naming of data object references and uniform data access. The uniform naming format includes a first field, representing an object type, and a second field, representing an object location of the form: <type>:<type-specific locator>. For example, an avaki object would be represented by: Avaki:/path/to/object and a DAV object would be represented by: DAV:http://davhost:port/path/to/object. The abstraction layer also provides for a generic constructor which delegates to a subconstructor either a data access or data storage process. The subconstructor is based on the object type of the data object. Uniform data access allows the user to store and retrieve data of various types including strings, byte arrays and data streams. To construct data objects in the data repository 40, the user or GUI 25 invokes: DataObj o=DataObj.create ("<type>:<type-specific locator>"). Parsing of this data object results in type="<type>" and rest="<type-specific locator>". Using pseudocode, the underlying implementation is illustrated in Table 4.

TABLE 4

DataObj DataObj.create(fullpath)
{ type=<everything to first colon>
rest=<everything after first colon>
// call type-specific constructor, passing it rest
return new <type>DataObj(rest)}
Parsing the data object illustrated in Table 4 results in, type = "<everything to first
colon>" and rest = "<everything after first colon>".

After creating the components and computer dataflow, the user must submit, to the master computer 10, the computer dataflow and the data files, stored in the data repository 40. The master computer 10 executes the dataflow on the worker computer(s) 50 by decomposing the dataflow into its constituent components and submitting the components to worker computer(s) 50 as tasks. The worker computers then fetch the components from the component library 30 for execution.

A taskbag abstraction layer manages the scheduling and communication of tasks and results between the master computer 10 and worker computers 50. The abstraction layer, shown in Table 5, is stored in the VMS 60.

TABLE 5

Taskbag creation methods
Taskbag Tb=Taskbag.create(name)
Taskbag Tb=Taskbag.createNew( )
Submission methods
id=Tb.submit(task)
result=Tb.getResult(id) // get result for task id
result=Tb.getResult( ) // get any result
Worker methods
(task=Tb.getTask( ) // retrieve a task to work on
Tb.putResult(result) // put the result back Encoded within the abstraction layer is scheduling logic for selection of the worker computer 50 to perform the given task where a task is comprised of a component and its input. The abstraction layer also includes code for communication logic which indicates how to transmit the task and results between the master computer 10 and worker computers 50. To execute a dataflow, the master computer 10 may submit a task to the taskbag abstraction layer without providing, to the taskbag abstraction layer, scheduling information for the submitted task or communication information for the results of the submitted task. The worker computer 50 retrieves the task from the abstraction layer, without obtaining scheduling information, from the taskbag abstraction layer, for the submitted task or communication information for the results of the submitted task. System 1 may include different taskbag abstraction layers to allow the simultaneous execution of different scheduling plans and communication mechanisms. Taskbag abstraction layers may be written using databases, virtual shared memory (e.g., JavaSpaces, Linda) or distributed object models (e.g., Corba, EBJ).

The method for executing dataflows, in accordance with the present invention, also provides for the execution of components in parallel through the automatic distribution of the components across a plurality of worker computers 50. To perform this parallel processing, the component may begin to process the data input upon receiving a minimum number of data elements rather than waiting to process the entire data input. Additionally, the component may produce a minimum number of data elements before completing the entire data input. After producing data elements, the elements will be passed to the next component for processing. For example, assume the dataflow is comprised of component A and component B. The initial data input is comprised of a data set with ten numbers of equal values $V_1$. Component A will transform each $V_1$ to $V_2$. When component A has transformed a minimum number of values $V_2$, Component B will begin to process values $V_2$.

Figure 5:
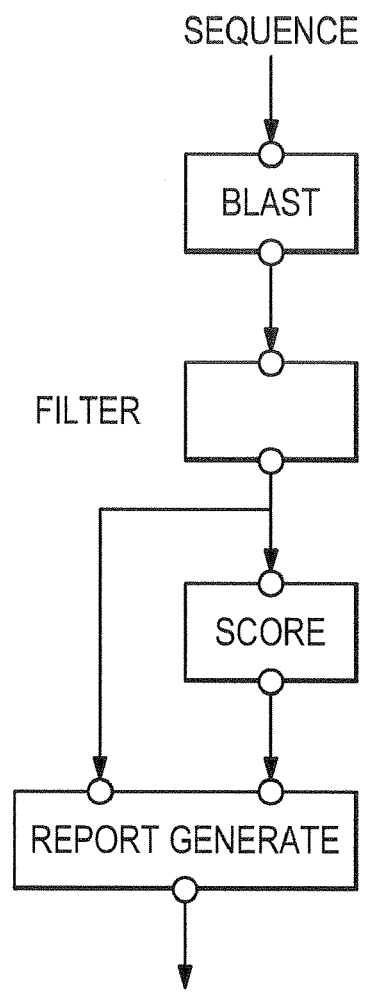
FIG. 5 is a flow chart illustrating a method of a preferred embodiment of the present invention.

The method of the present invention may also include the conditional execution of components where data satisfying a condition is written to a selected data input. Data that fails to satisfy a condition is written to a different data input. FIG. 5 illustrates a dataflow comprised of Blast, filter, score and report generate components. The filter component writes data, which satisfies a score threshold from the Blast component, to an input pin of the report generate component. Data which is below the score threshold is written to an input pin of the score component.

The method for executing dataflows, in accordance with the present invention, also provides for the execution of components by parallel replication. To perform parallel replication, a component is replicated and multiple copies of the component are stored in the component library 30. When a worker computer 50 obtains a task from a central task list, the worker computer 50 then fetches a copy of the necessary component from the component library 30 and then processes the data input. For example, component A takes a large problem and divides the problem into a number of independent sub-problems. The sub-problems are then processed on component B in parallel on different sets of worker computers 50 where each worker computer 50 has its own copy of component B which the worker obtained from the component library 30.

This parallel replication method also applies when a speed mismatch between a pair of adjacent dataflow components exists. If the upstream component is faster, than the downstream component, it will likely produce outputs more rapidly than the downstream component can process the inputs. The worker computers 50 will recognize that there are many independent sets of data input awaiting processing by the downstream component. The plurality of worker computers 50 will automatically replicate the downstream component, by fetching the downstream component from the component library 30, and then processing the data input.

The methods described above for parallel processing or parallel replication also apply to the processing of multiple dataflows when more than one dataflow is submitted to the system 1.

The execution of components is facilitated by a component interpreter abstraction layer which examines the component name and the inputs and outputs associated with the component. The component interpreter abstraction layer then selects and invokes a sub-interpreter based on the component's name, inputs and outputs and metadata. The selected sub-interpreter then executes the underlying component using the component's metadata and inputs and outputs.

Figure 6:
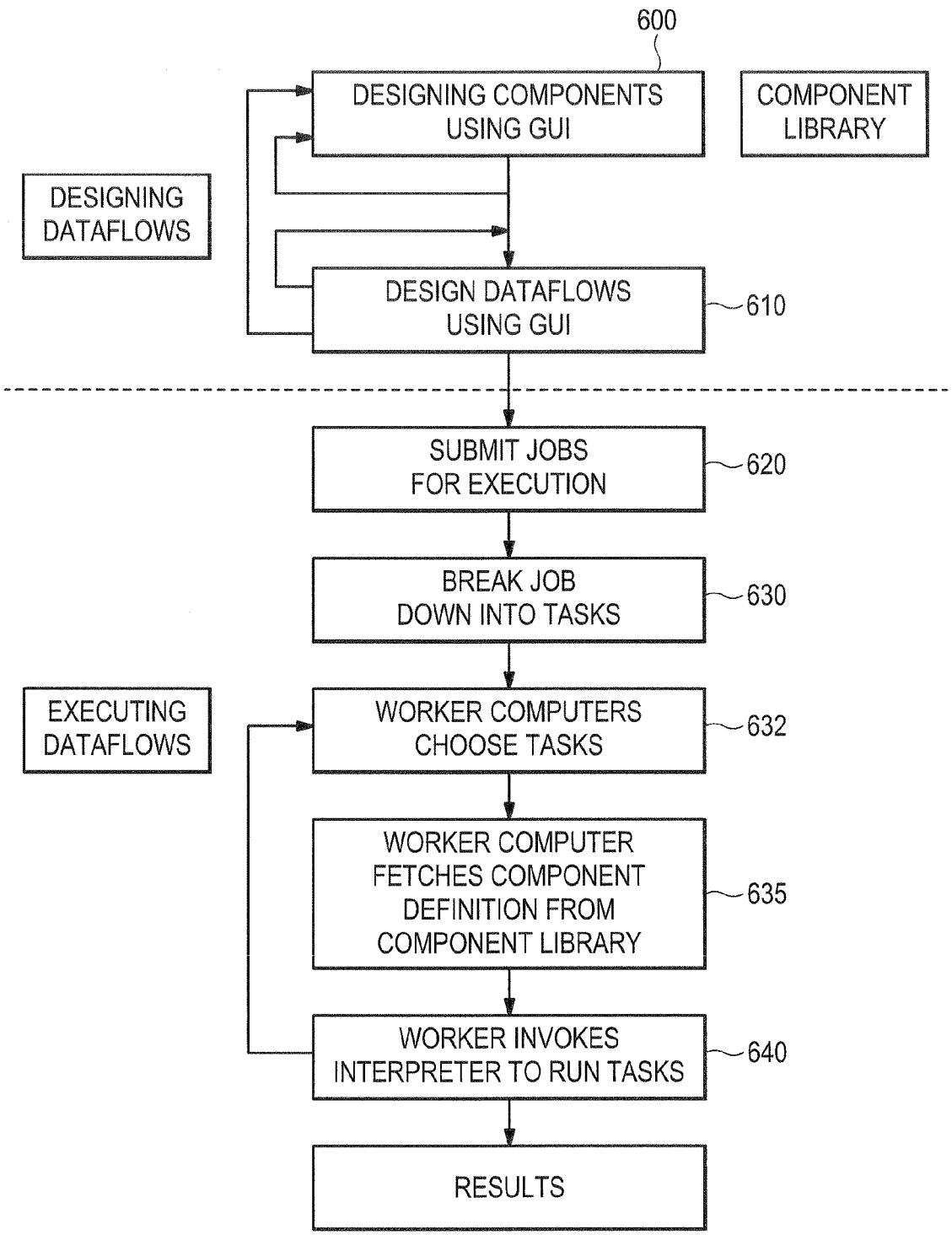
FIG. 6 is a flow chart illustrating a method of a preferred embodiment of the present invention.

With reference to FIG. 6, a flow chart illustrating a preferred embodiment of the method of the present invention is shown. In step 600, an component is defined, based on an input, an output, metadata and a sub-interpreter, using a graphical user interface 25. Each component represents a computer-implemented computational process that is performed on one or more inputs to the component. The computer-implemented computational process generates one or more outputs based on a predefined computational algorithm. This step is repeated until the user has created all the necessary components. In step 610, the user visually creates the computer dataflow on a user display using a graphical user interface 25. The user selects components, from the component library 30 of components, and graphically connects one or more input terminals of selected components with one or more output terminals of selected components. Each selected component and the one or more input terminals graphically correspond to the one or more inputs to the predefined computational algorithm associated with the component. The one or more output terminals graphically correspond to the one or more outputs generated by the predefined computational algorithm associated with the component. This step is repeated until the user has selected and connected the components needed to complete the dataflow. In step 620, a job is submitted by a master computer 10 and in step 630 breaks down the job into tasks where a task is a component and its data input. In step 632, the worker computer 50 chooses a task and in step 635 the worker computer 50 fetches the appropriate component and its arguments from the component library 30. In step 640, the work computer 50 invokes the appropriate sub-interpretation to process the task. When the worker computer 50 completes step 640, steps 632-640 are repeated until there are no remaining unprocessed tasks. Table 6 illustrates pseudocode for a worker computer (50).

TABLE 6

```
do forever { Task t = Tb.getTask( )
    Component c = task.getComponentDef( )
    Interpreter i = c.getSubInterpreter( )
    Result r = i.run(t, c)
    Tb.putResult(r)}
```

EXAMPLE 1

The following provides a detailed example applying the method of the present invention to a dataflow for a protein sequence classification. An important problem for many bioinformatics researchers is the classification of groups of amino-acid sequences into fine-grained categories (subfamilies) whose members have similar physical properties and may be metabolically related. For example, each of the sequences involved might be what is known as a structural domain of some protein in a certain protein family, and the goal might be to identify which of the sequences are likely to have similar function. For a typical problem, there may be tens of thousands of sequences involving millions of amino acids.

A number of approaches to this sequence classification problem are possible, but the one considered here creates the subfamilies by identifying "seed pairs" (highly similar pairs of sequences) and collecting other sequences around each seed pair based on a model of the nature of the similarity of the pair. Stated more precisely, the computation proceeds in a series of steps. First, find a number of disjoint, highly similar pairs of sequences and designate each as the seed pair for a new subfamily. Second, create a model that captures the nature of the similarities among all the sequences in the subfamily. This model will be used to measure the similarity between the subfamily and any arbitrary sequence. For this example, the model will be what is known as a Hidden Markov Model (HMM), and the measurement process for an arbitrary sequence will assign to that sequence a score indicating the likelihood that the sequence should be placed in the subfamily. Third, assess all the sequences against each subfamily model, and assign each sequence to the subfamily for which it achieves the highest score. Repeat Steps 2 and 3 using the new set of subfamilies.

The above approach to solving the sequence classification problem, although straightforward to describe, involves a significant number of computationally intensive steps. Each step requires the use of a particular bioinformatics program, and some of the steps are very time consuming. The required bioinformatics programs are: BLASTP, a program from the National Center for Biotechnology Information (NCBI) that can rapidly assess the similarity of pairs of protein sequences and is used to find seed pairs in Step 1; CLUSTALW, another program from the NCBI that aligns two or more protein or DNA sequences so as to maximize the match between the aligned sequences and is used to create the model for each seed pair in Step 2; HMMBUILD, a program that creates a hidden Markov model that describes a set of aligned sequences and is used in Step 2; HMMCALIBRATE, a program that optimizes hidden Markov models created by HMMBUILD and is used in Step 2; and HMMSEARCH, a program that scores the sequences in large sequence databases against a calibrated hidden Markov model and is used for sequence assessment in Step 3.

Although System 1 contains pre-built components for programs such as FORMATDB, BLASTALL, CLUSTALW, HMMBUILD, HMMCALIBRATE, and HMMSEARCH, the user must create additional components built specifically for the sequence classification dataflow. One such component is a script component, "FamilyFilter," encapsulating the Perl script used to select the seed pairs and create the initial set of subfamilies based on the BLASTP output in Step 2 of the dataflow. GUI 25 is used to define the interface for a component, using "pins" to represent the input and output data and mapping the pins to the corresponding variable names used in the Perl script itself. For the FamilyFilter component, the inputs will be the output of BLASTP in fasta format and a set of parameters (such as the number of seed pairs to select), and the output will be a dataset describing the seed pairs as a group.

In addition to the "Family Filer" component, two other special components are required for the sequence classification dataflow. The first of these components splits a single dataset describing a group of subfamilies into separate datasets describing each subfamily. The second reverses this process by combining a number of separate datasets describing individual subfamilies into a single dataset describing all of the subfamilies as a group. These "FamilySplitter" and "FamilyJoiner" components are used to increase the potential for parallel processing in the dataflow by creating independent subproblems and combining the results into a single solution, respectively. System 1 can replicate the components in the "parallelizable section" (between the FamilySplitter and FamilyJoiner components) in order to increase performance.

Figure 7:
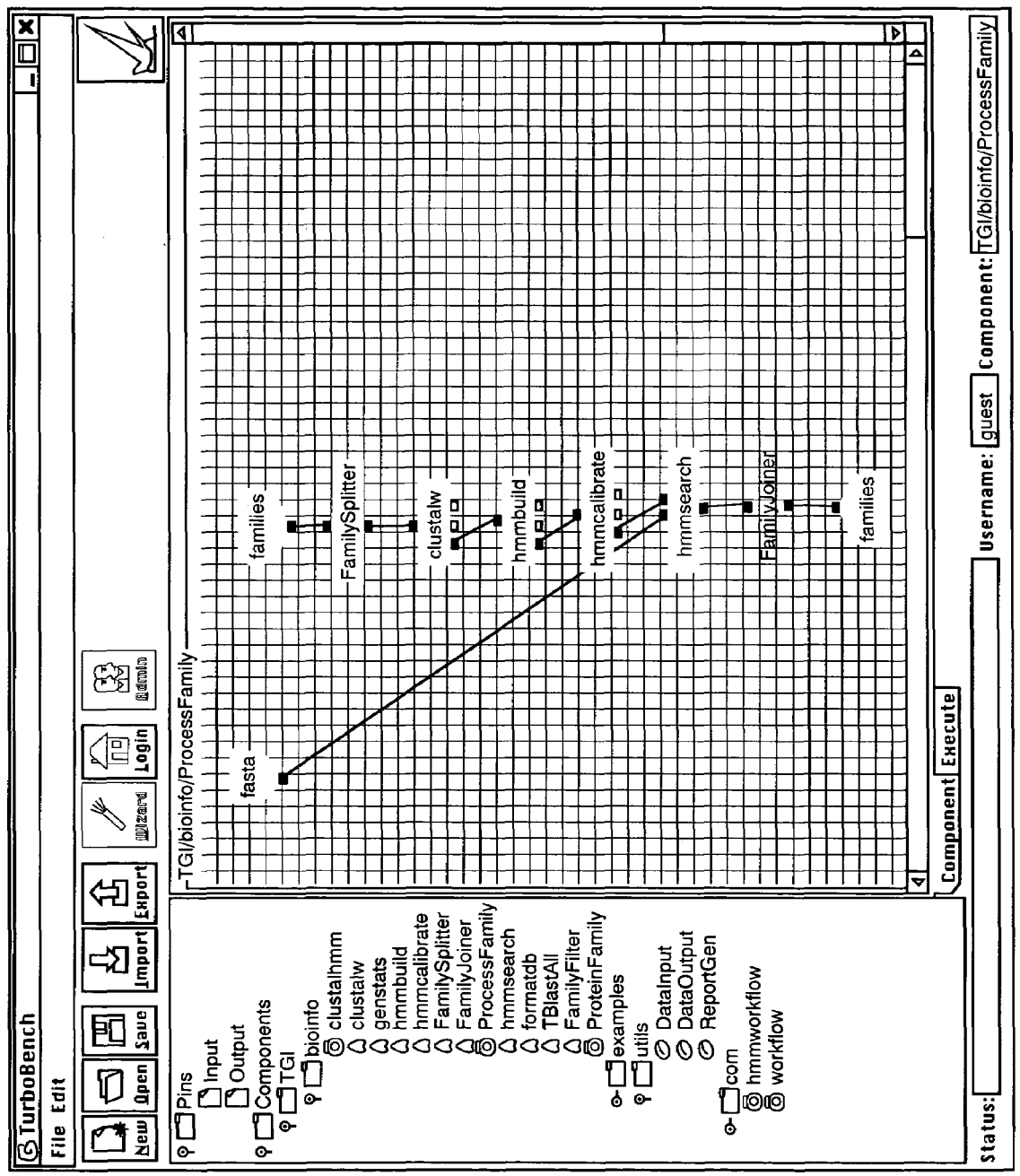
FIG. 7 illustrates an exemplary dataflow in connection with the present invention.
Figure 8:
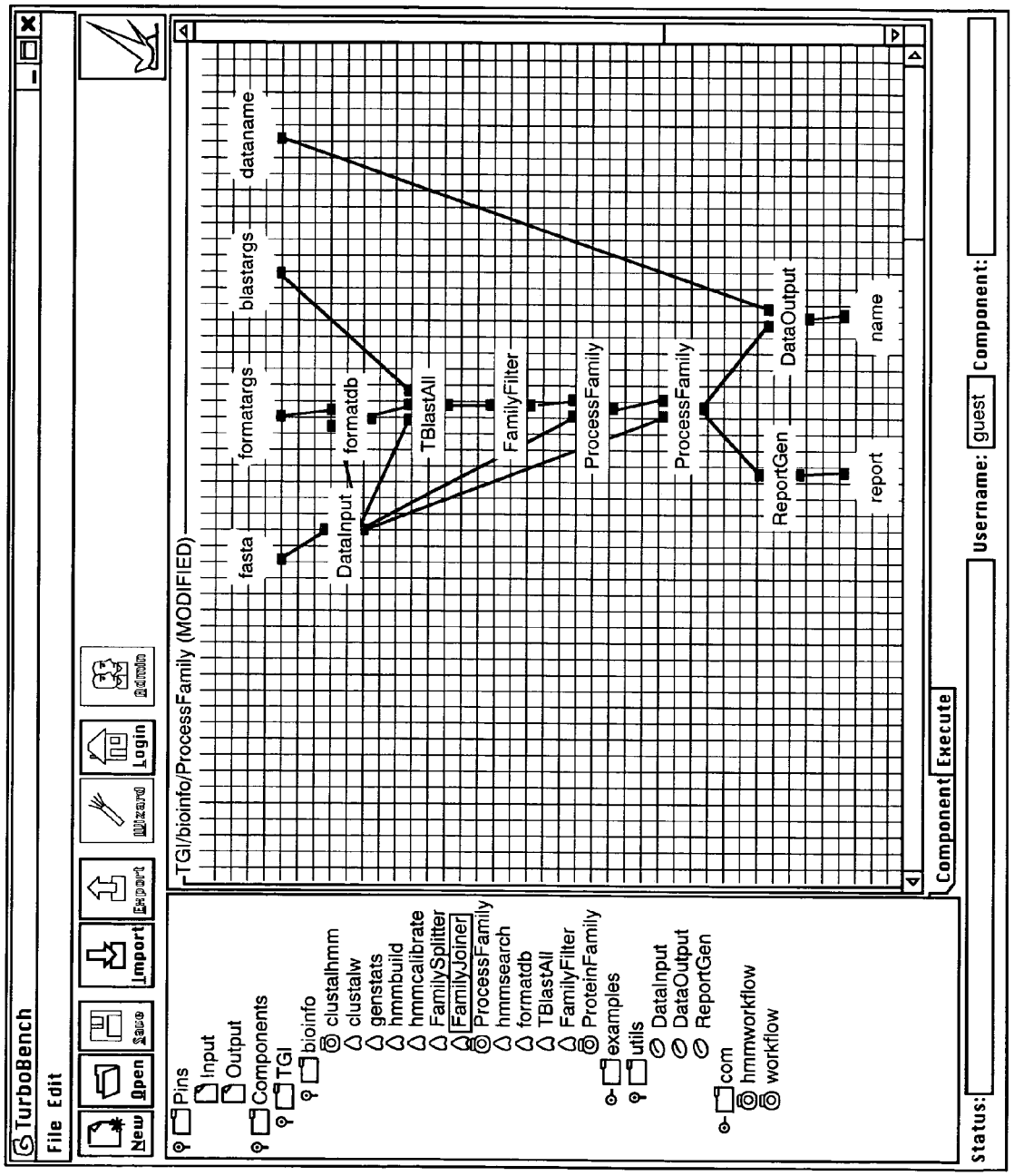
FIG. 8 illustrates an exemplary dataflow in connection with the present invention.

Once all the required components are available in the component library 30, the GUI 25 may be used to create the dataflow that will implement the sequence classification computation. Using the GUI 25, the dataflow is created visually by dragging and dropping computational components onto the design panel, creating data components corresponding to the various input and output data, and then indicating the flow of data among components by drawing data flow lines between component pins. FIG. 7 and FIG. 8 depict the GUI 25 interface for dataflow creation of the "ProcessFamily" and "ProteinFamily" dataflows, respectively.

Dataflows constitute a type of component in system 1. As a result, system 1 enables a hierarchical design process in which complex dataflows may be built up from simpler dataflows. For the sequence classification dataflow, a dataflow is created corresponding to the part of the sequence classification dataflow that takes one group of subfamilies and computes a new group of subfamilies to replace the original set (Steps 3 -7 of the overall dataflow). FIG. 7 shows the "ProcessFamily" dataflow component.

The ProcessFamily component has two inputs: a dataset containing all of the sequences in fasta format, and a dataset describing a group of subfamilies. The component has just one output; a dataset describing the set of subfamilies that result from Steps 3-7 of the dataflow.

Each step of the dataflow in the ProcessFamily component is described below to understand the operation of this component. FamilySplitter component takes a single input dataset describing a group of subfamilies and creates multiple output datasets, one describing each of the subfamilies in the group. Each of the output datasets is passed on independently for processing by the next component in the dataflow (CLUSTALW). The CLUSTALW component takes as its input a dataset describing the sequences in a subfamily and performs a multiple alignment of those sequences. The CLUSTALW output is passed to the HMMBUILD component, which creates a Hidden Markov Model that is then passed to the HMMCALIBRATE component for calibration. The HMMSEARCH component then takes the result of HMMCALIBRATE and creates a score for each of the original input sequences against the calibrated model. Finally, the FamilyJoiner component waits until all the HMMSEARCH results are complete and then forms a new group of families by assigning each sequence to the family whose hidden Markov model has given it the highest score. The output of FamilyJoiner is a single dataset containing data describing the new group of subfamilies.

The ProcessFamily dataflow component is built using GUI 25. When complete, that component is saved in the component library 30, whose contents are shown in the lefthand panel of the GUI 25 (see FIG. 7). The dataflow for sequence classification, "ProteinFamily," is created using the ProcessFamily component in combination with other standard components available already in system 1. The full dataflow, "ProteinFamily," is shown in FIG. 8.

The ProteinFamily dataflow component has four inputs: the name of the dataset containing all of the sequences to be classified; separate inputs containing arguments for FORMATDB and TBLASTALL, respectively; and the name to be used for the dataset containing the final result, which is the description of the optimized group of subfamilies. ProteinFamily also has two outputs: a report delivered in html for viewing in a web browser; and the name of the dataset containing the final results.

To understand the operation of the ProteinFamily dataflow, each component is discussed below and illustrated in FIG. 8. The first step is performed by the DATAINPUT component, which uses the dataset name provided as input to retrieve (via the data repository 40) the actual dataset containing the sequences in fasta format. Next, the FORMATDB component converts the fasta data into the database format used by BLAST, guided by the formatting parameters provided as a second input. The BLAST database format consists of several related files stored in a single directory. The entire directory is passed on to the TBLASTALL component, along with the original set of sequences and a number of parameters to control the operation of BLAST. The TBLASTALL component is used to perform an "all-to-all" BLASTP computation.

The BLAST results are then passed to FamilyFilter, the user-created script component that selects a number of disjoint pairs of highly similar sequences to be the seeds for the initial group of subfamilies. This process entails removing identity matches (scores for a sequence matching itself), sorting the remaining matches by e-value score, removing multiple matches for each sequence, selecting the proper number of seed pairs, and creating a description (in XML) of the resulting group of subfamilies.

The output from FamilyFilter is now fed twice through the ProcessFamily dataflow—once for each pass through Steps 3-7 of the original dataflow. In the first pass, each subfamily contains just a seed pair, while, in the second pass, each family contains all the sequences assigned to it during the first invocation of ProcessFamily. Finally, the group of subfamilies emerging from the second invocation of ProcessFamily is passed on both to the REPORTGEN component, which generates the html report, and to the DATAOUT component that stores the subfamily data in the data repository 40.

Before actually running the ProteinFamily dataflow, the input data is installed in the data repository 40. For the ProteinFamily dataflow, only the FASTA input sequences are stored in the data repository 40, since the other inputs may be entered directly when the dataflow is run.

The present invention may be embodied in other specific forms without departing from the spirit or essential attributes of the invention. Accordingly, reference should be made to the appended claims, rather than the foregoing specification, as indicating the scope of the invention. Although the foregoing description is directed to the preferred embodiments of the invention, it is noted that other variations and modifications will be apparent to those skilled in the art, and may be made without departing from the spirit or scope of the invention.

What is claimed:

1. A method for creating and executing a computer dataflow, comprising:
    (a) defining a plurality of components based on an input, an output, metadata and a sub-interpreter, each of said components representing a computer-implemented computational process that is performed on one or more inputs to the component and that generates one or more outputs based on a predefined computational algorithm;
    (b) providing a graphical user interface that allows a user to visually create the computer dataflow on a user display by selecting one or more components from a library of said components, and graphically connecting one or more input terminals of a first of the selected components with one or more output terminals of at least a second of the selected components;
    where, for each selected component, the one or more input terminals graphically correspond to the one or more inputs to the predefined computational algorithm associated with the component, and the one or more output terminals graphically correspond to the one or more outputs generated by the predefined computational algorithm associated with the component; and
    (c) without intervention from the user, distributing execution of the plurality of said selected components across a plurality of machines during performance of the computer dataflow;
    where the selected component automatically executes upon receiving a minimum number of inputs;

where the metadata associated with each of the plurality of components is configured to describe at least one of the input, the output, the sub-interpreter, and data files of each of the associated components; and where the sub-interpreter associated with each of the plurality of components is configured to describe at least the computational algorithm invoked during execution of the associated component.

2. The method of claim 1, comprising making the component at least one of a command line component, a java component, a jython component, or a dataflow component.

3. The method of claim 1, comprising using the predefined computational algorithm to solve computations in at least one of biotechnology, pharmaceutical, geophysical, engineering, chemistry, automotive, aerospace, or finance disciplines.

4. The method of claim 1, where the distributing comprises each machine selecting a task from a central task list.

5. The method of claim 1, comprising executing the component without accessing a source code.

6. The method of claim 1, where scripting is not required to create the computer dataflow.

7. The method of claim 1, where manual data reformatting is not required.

8. The method of claim 1, comprising using the computer dataflow to solve a bioinformatics computational analysis.

9. The method of claim 1, comprising using the computer dataflow to solve a clinical medicine computational analysis.

10. A method for creating and executing a computer dataflow, comprising:
   (a) defining a plurality of components based on an input, an output, metadata and a sub-interpreter, each of said components representing a computer-implemented computational process that is performed on one or more inputs to the component and that generates one or more outputs based on a predefined computational algorithm; and
   (b) providing a graphical user interface that allows a user to visually create the computer dataflow on a user display by selecting from a library of said components, and graphically connecting one or more input terminals of selected components with one or more output terminals of other selected components;
   where, for each selected component, the one or more input terminals graphically correspond to the one or more inputs to the predefined computational algorithm associated with the component, and the one or more output terminals graphically correspond to the one or more outputs generated by the predefined computational algorithm associated with the component;
   where, for at least one selected component, a selected output terminal of the component satisfies at least one condition associated with an input terminal of a first other component and the selected output terminal of the component fails to satisfy the condition to another input terminal of a third component;
   where the metadata associated with each of the plurality of components is configured to describe at least one of the input, the output, the sub-interpreter, and data files of each of the associated components; and
   where the sub-interpreter associated with each of the plurality of components is configured to describe at least the computational algorithm invoked during execution of the associated component.

11. The method of claim 10, comprising making the component at least one of a command line component, a java component, a jython component, or a dataflow component.

12. The method of claim 10, comprising using the predefined computational algorithm to solve computations in at least one of biotechnology, pharmaceutical, geophysical, engineering, chemistry, automotive, aerospace, or finance disciplines.

13. The method of claim 10, comprising establishing a threshold value for the condition.

14. The method of claim 10, comprising executing the component using the plurality of machines without accessing a source code.

15. The method of claim 10, where scripting is not required to create the computer dataflow.

16. The method of claim 10, where manual reformatting of data is not required.

17. The method of claim 10, comprising using the computer dataflow to solve a bioinformatics computational analysis.

18. The method of claim 10, comprising using the computer dataflow to solve a clinical medicine computational analysis.

19. A method for executing a computer dataflow that accesses and stores data to and from a plurality of different systems, where each of the different systems uses a different mechanism for accessing and storing data, comprising:
   (a) defining a data repository abstraction layer that is used by the computer dataflow, where the abstraction layer provides a uniform naming format for each of the different mechanisms for accessing and storing data and the uniform naming format includes a first field representing an object type and a second field representing an object location;
   (b) during creation of the computer dataflow, defining data object references by a graphical user interface where each data object reference has object type as a data format and object location as a physical location;
   (c) during execution of the computer dataflow, interpreting each data object in the dataflow that is represented in accordance with the uniform naming format; and
   (d) delegating, with a generic constructor and based on the interpreting, either an access or storage process associated with the data object to a subconstructor that corresponds to the object type of the data object.

20. The method of claim 19, where comprising using the computer dataflow to solve a bioinformatics computational analysis.

21. The method of claim 19, where comprising using the computer dataflow to solve a clinical medicine computational analysis.

22. A method for executing a computer dataflow in which a plurality of master entities submit tasks to be performed, and a plurality of worker entities perform tasks submitted by the master entities, comprising:
   (a) defining a taskbag abstraction layer that interacts between the master entities and the worker entities, where scheduling logic for selecting which worker should perform a given task is coded in the taskbag abstraction layer, and communication logic indicating how results should be transmitted between a worker entity and a master entity associated with the given task are also coded in the taskbag abstraction layer;
   (b) during execution of the dataflow, submitting by a master entity a task to the taskbag abstraction layer without providing information to the taskbag abstraction layer indicating how to schedule the submitted task or transmit results of the submitted task; and
   (c) during execution of the dataflow, retrieving by a worker entity a task from the taskbag abstraction layer without retrieving from the taskbag abstraction layer information indicating how to schedule the retrieved task or transmit results of the retrieved task.

23. The method of claim 22, where the worker entity executes the task without accessing a source code.

24. The method of claim 22, where manual reformatting of data between each of the defining, submitting, and retrieving is not required.

25. The method of claim 22, comprising using the computer dataflow to solve a bioinformatics computational analysis.

26. The method of claim 22, where comprising using the computer dataflow to solve a clinical medicine computational analysis.

27. A method for executing a computer dataflow that accesses and stores data to and from a plurality of different systems, where each of the different systems uses a different representation of data and optionally a different mechanism for accessing and storing data, comprising:
   (a) defining a plurality of components, each of the components representing a computer-implemented computational process that is performed on one or more inputs to the component and that generates one or more outputs based on a predefined computational algorithm;
   (b) defining a uniform description format for each of the different representations of data and the different mechanisms for accessing and storing data, where the uniform description format includes a field representing data type;
   (c) providing a graphical user interface that allows a user to visually create the computer dataflow on a user display by selecting from a library of said components, and graphically connecting one or more input terminals of selected components with one or more output terminals of second selected components;
   where, for each selected component, the one or more input terminals graphically correspond to the one or more inputs to the predefined computational algorithm associated with the component, and the one or more output terminals graphically correspond to the one or more outputs generated by the predefined computational algorithm associated with the component;
   (d) where, if one or more inputs of a selected component has a data type that does not match one or more outputs of the selected component, the graphical user interface determines whether a corresponding converter exists; and
   (e) if a corresponding converter does not exist, the graphical user interface is configured to indicate a data mapping between at least one input data type and at least one output data type at creation of the computer dataflow.

28. The method of claim 27, comprising making the component at least one of a command line component, a java component, a jython component, or a dataflow component.

29. The method of claim 27, comprising using the predefined computational algorithm to solve computations in at least one of biotechnology, pharmaceutical, geophysical, engineering, chemistry, automotive, aerospace, or finance disciplines.

30. The method of claim 27, where scripting is not required to create the computer dataflow.

31. The method of claim 27, where manual reformatting of data between each of the defining the plurality of components, defining the uniform description format, and providing is not required.

32. The method of claim 27, comprising using the computer dataflow to solve a bioinformatics computational analysis.

33. The method of claim 27, comprising using the computer dataflow to solve a clinical medicine computational analysis.

34. A method for creating and executing a computer dataflow, comprising:
   (a) defining a plurality of components based on an input, an output, metadata and a sub-interpreter, each of said components representing a computer-implemented computational process that is performed on one or more inputs to the component and that generates one or more outputs based on a predefined computational algorithm;
   (b) providing a graphical user interface that allows a user to visually create the computer dataflow on a user display by selecting from a library of said components, and graphically connecting one or more input terminals of selected components with one or more output terminals of second selected components;
   where, for each selected component, the one or more input terminals graphically correspond to the one or more inputs to the predefined computational algorithm associated with the component, and the one or more output terminals graphically correspond to the one or more outputs generated by the predefined computational algorithm associated with the component; and
   (c) defining a component interpreter abstraction layer that facilitates execution of a component by examining a name of the component, the one or more inputs and the one or more outputs associated with the component, and then selecting and invoking a sub-interpreter based on the name of the component, the one or more inputs and the one or more outputs associated with the component;
   (d) without intervention from the user, distributing execution of the plurality of said selected components across a plurality of machines during performance of the computer dataflow, where the component automatically executes upon receiving a minimum number of inputs; and
   (e) executing, with the sub-interpreter, the component using the input, output and metadata
   where the metadata associated with each of the plurality of components is configured to describe at least one of the input, the output, the sub-interpreter, and data files of each of the associated components.

35. The method of claim 34, where comprising making the component at least one of a command line component, a java component, a jython component, or a dataflow component.

36. The method of claim 34, comprising using the predefined computational algorithm to solve computations in at least one of biotechnology, pharmaceutical, geophysical, engineering, chemistry, automotive, aerospace, or finance disciplines.

37. The method of claim 34, where the distributing comprises each machine selecting a task from a central task list.

38. The method of claim 34, comprising executing the component using the plurality of machines without accessing a source code.

39. The method of claim 34, where scripting is not required to create the computer data flow.

40. The method of claim 34, where manual reformatting of data between at least each of the defining the plurality of components, providing the graphical user interface, defining the component interface, distributing the execution, and executing the component is not required.

41. The method of claim 34, comprising using the computer dataflow to solve a bioinformatics computational analysis.

42. The method of claim 34, comprising using the computer dataflow to solve a clinical medicine computational analysis.

43. A system, comprising:
- a library storing a plurality of components each including one or more inputs, one or more outputs, metadata and a sub-interpreter, each component representing a computer-implemented computational process that is performed on the one or more inputs to generate the one or more outputs based on a predefined computational algorithm;
- a graphical user interface that allows a user to visually create a computer dataflow on a display by selecting one or more components stored in the library and graphically connecting one or more inputs of a first selected component with one or more outputs of at least a second selected component;
- a master computer configured to distribute execution of the selected one or more components to one or more worker computers without intervention from the user during performance of the computer dataflow;
- where the one or more selected component automatically executes upon receiving a minimum number of inputs;
- where the metadata associated with each of the plurality of components is configured to describe at least one of the one or more inputs, the one or more outputs, the sub-interpreter, or data files associated with any of the one or more of the selected components; and
- where the sub-interpreter associated with each of the plurality of components is configured to describe at least the predefined computational algorithm.

44. An apparatus, comprising:
- a memory configured to store instructions; and
- a processor configured to execute the instructions stored in the memory to:
  - receive a computer dataflow created using a graphical interface by selecting one or more components stored in a library and graphically connecting one or more inputs of a first selected component with one or more outputs of at least a second selected component;
  - distribute execution of the selected one or more components to one or more worker computers without user intervention during performance of the computer dataflow;
- where each of the one or more components stored in the library include one or more inputs, one or more outputs, metadata and a sub-interpreter, each component representing a computer-implemented computational process that is performed on the one or more inputs to generate the one or more outputs based on a predefined computational algorithm;
- where the one or more selected component automatically executes upon receiving a minimum number of inputs;
- where the metadata associated with each of the plurality of components is configured to describe at least one of the one or more inputs, the one or more outputs, the sub-interpreter, or data files associated with any of the one or more of the selected components; and
- where the sub-interpreter associated with each of the plurality of components is configured to describe at least the predefined computational algorithm.

45. A tangible computer-readable medium, having stored thereon, computer-executable instructions, that, if executed by a machine, cause the machine to perform a method comprising:
- defining a plurality of components based on an input, an output, metadata and a sub-interpreter, each of said components representing a computer-implemented computational process that is performed on one or more inputs to the component and that generates one or more outputs based on a predefined computational algorithm;
- providing a graphical user interface that allows a user to visually create the computer dataflow on a user display by selecting one or more components from a library of said components, and graphically connecting one or more input terminals of a first of the selected components with one or more output terminals of at least a second of the selected components; and
- without intervention from the user, distributing execution of the plurality of said selected components across a plurality of machines during performance of the computer dataflow;
- where, for each selected component, the one or more input terminals graphically correspond to the one or more inputs to the predefined computational algorithm associated with the component, and the one or more output terminals graphically correspond to the one or more outputs generated by the predefined computational algorithm associated with the component;
- where the selected component automatically executes upon receiving a minimum number of inputs;
- where the metadata associated with each of the plurality of components is configured to describe at least one of the input, the output, the sub-interpreter, and data files of each of the associated components; and
- where the sub-interpreter associated with each of the plurality of components is configured to describe at least the computational algorithm invoked during execution of the associated component.

46. A tangible computer-readable medium, having stored thereon, computer-executable instructions, that, if executed by a machine, cause the machine to perform a method comprising:
- defining a plurality of components, each of the components representing a computer-implemented computational process that is performed on one or more inputs to the component and that generates one or more outputs based on a predefined computational algorithm;
- defining a uniform description format for each of one or more distinct representations of data and one or more distinct mechanisms for accessing and storing data, where the uniform description format includes a field representing data type;
- providing a graphical user interface that allows a user to visually create a computer dataflow by selecting from a library of the plurality of components, and graphically connecting one or more inputs of selected components with one or more outputs of second selected components;
- if one or more inputs of a selected component has a data type that does not match one or more outputs of the selected component, determining whether a corresponding converter exists; and
- if a corresponding converter does not exist, indicating a data mapping between at least one input data type and at least one output data type at creation of the computer dataflow;
- where, for each selected component, the one or more inputs graphically correspond to the one or more inputs to the predefined computational algorithm associated with the component, and the one or more outputs graphically correspond to the one or more outputs generated by the predefined computational algorithm associated with the component.

* * * * *

UNITED STATES PATENT AND TRADEMARK OFFICE
CERTIFICATE OF CORRECTION

PATENT NO.      : 7,614,036 B2                                          Page 1 of 1
APPLICATION NO. : 10/610133
DATED           : November 3, 2009
INVENTOR(S)     : Bjornson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1688 days.

Signed and Sealed this

Nineteenth Day of October, 2010

David J. Kappos
*Director of the United States Patent and Trademark Office*